United States Patent
Volpe et al.

(10) Patent No.: US 12,303,706 B2
(45) Date of Patent: *May 20, 2025

(54) SYSTEM AND METHOD FOR CONSERVING POWER IN A MEDICAL DEVICE

(71) Applicant: ZOLL Medical Corporation, Chelmsford, MA (US)

(72) Inventors: Shane S. Volpe, Saltsburg, PA (US); Richard A. Rattanni, Verona, PA (US); Thomas E. Kaib, Irwin, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 103 days.

This patent is subject to a terminal disclaimer.

(21) Appl. No.: 18/297,104

(22) Filed: Apr. 7, 2023

(65) Prior Publication Data
US 2023/0310874 A1     Oct. 5, 2023

Related U.S. Application Data

(63) Continuation of application No. 16/655,440, filed on Oct. 17, 2019, now Pat. No. 11,648,412, which is a
(Continued)

(51) Int. Cl.
*A61N 1/39* (2006.01)
*A61B 5/352* (2021.01)
(Continued)

(52) U.S. Cl.
CPC ............ *A61N 1/3987* (2013.01); *A61B 5/352* (2021.01); *A61N 1/3925* (2013.01);
(Continued)

(58) Field of Classification Search
CPC .. A61N 1/0484; A61N 1/3925; A61N 1/3993; A61N 1/3987; A61N 1/365; A61N 1/36135
See application file for complete search history.

(56) References Cited

U.S. PATENT DOCUMENTS 3,553,651 A    1/1971  Bird et al.
4,576,170 A    3/1986  Bradley et al.
(Continued)

FOREIGN PATENT DOCUMENTS

JP    2002-514107 A    5/2002
JP    2008-302228 A    12/2008
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.
(Continued)

*Primary Examiner* — Alyssa M Alter
(74) *Attorney, Agent, or Firm* — Finch & Maloney PLLC

(57) ABSTRACT

A system and method for conservation of battery power in a portable medical device is provided. In one example, a processor arrangement includes a dual core processor having an ARM core and a DSP core. The portable medical device includes a monitor having the dual core processor, in communication with a belt node processor. The DSP core receives physiological data from the physiological sensor and sends the physiological data to the ARM core. The ARM core analyzes the physiological data to determine if a treatment sequence is necessary. The DSP core receives physiological data from the at least one physiological sensor and sends the physiological data to the ARM core, and also analyzes the physiological data to determine proper timing of the treatment sequence by the at least one therapy delivery device to synchronize at least one pulse of the treatment sequence with the physiological data.

19 Claims, 14 Drawing Sheets

Related U.S. Application Data continuation of application No. 15/212,993, filed on Jul. 18, 2016, now Pat. No. 10,493,289, which is a continuation-in-part of application No. 14/974,794, filed on Dec. 18, 2015, now Pat. No. 9,454,219, which is a continuation of application No. 14/531,794, filed on Nov. 3, 2014, now abandoned, which is a continuation of application No. 12/833,096, filed on Jul. 9, 2010, now Pat. No. 8,904,214.

(51) Int. Cl.
  *G06F 1/3203* (2019.01)
  *G06F 1/3234* (2019.01)
  *G06F 1/324* (2019.01)
  *G06F 1/3293* (2019.01)
  *G06F 1/3296* (2019.01)
  *G06F 9/54* (2006.01)
  *G16H 20/30* (2018.01)
  *G16H 40/63* (2018.01)
  *A61N 1/04* (2006.01)

(52) U.S. Cl.
  CPC ......... *A61N 1/3993* (2013.01); *G06F 1/3203* (2013.01); *G06F 1/324* (2013.01); *G06F 1/325* (2013.01); *G06F 1/3293* (2013.01); *G06F 1/3296* (2013.01); *G06F 9/542* (2013.01); *G16H 20/30* (2018.01); *G16H 40/63* (2018.01); *A61N 1/0484* (2013.01); *A61N 1/3975* (2013.01); *Y02D 10/00* (2018.01)

(56) References Cited

U.S. PATENT DOCUMENTS

| | | | |
|---|---|---|---|
| 4,580,572 A | 4/1986 | Granek et al. | |
| 4,583,547 A | 4/1986 | Granek et al. | |
| 4,729,377 A | 3/1988 | Granek et al. | |
| 4,928,690 A | 5/1990 | Heilman et al. | |
| 4,991,217 A | 2/1991 | Garrett et al. | |
| 5,078,134 A | 1/1992 | Heilman et al. | |
| 5,741,306 A | 4/1998 | Glegyak et al. | |
| 5,924,979 A | 7/1999 | Swedlow et al. | |
| 5,929,601 A | 7/1999 | Kaib et al. | |
| 5,944,669 A | 8/1999 | Kaib | |
| 6,065,154 A | 5/2000 | Hulings et al. | |
| 6,097,982 A | 8/2000 | Glegyak et al. | |
| 6,148,233 A | 11/2000 | Owen et al. | |
| 6,253,099 B1 | 6/2001 | Skin et al. | |
| 6,280,461 B1 | 8/2001 | Glegyak et al. | |
| 6,336,900 B1 | 1/2002 | Alleckson et al. | |
| 6,374,138 B1 | 4/2002 | Owen et al. | |
| 6,406,426 B1 | 6/2002 | Reuss et al. | |
| 6,546,285 B1 | 4/2003 | Owen et al. | |
| 6,681,003 B2 | 1/2004 | Linder et al. | |
| 6,889,078 B2 | 5/2005 | Struble et al. | |
| 6,889,079 B2 | 5/2005 | Bocek et al. | |
| 6,908,437 B2 | 6/2005 | Bardy | |
| 7,149,579 B1 | 12/2006 | Koh et al. | |
| 7,340,296 B2 | 3/2008 | Stahmann et al. | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,369,944 B2 | 2/2013 | Macho et al. | |
| 8,406,842 B2 | 3/2013 | Kaib et al. | |
| 8,644,925 B2 | 2/2014 | Volpe et al. | |
| 8,649,861 B2 | 2/2014 | Donnelly et al. | |
| 8,676,313 B2 | 3/2014 | Volpe et al. | |
| 8,706,215 B2 | 4/2014 | Kaib et al. | |
| 8,774,917 B2 | 7/2014 | Macho et al. | |
| 8,880,196 B2 | 11/2014 | Kaid | |
| 8,897,860 B2 | 11/2014 | Volpe et al. | |
| 8,904,214 B2 | 12/2014 | Volpe et al. | |
| 9,283,399 B2 | 3/2016 | Donnelly et al. | |
| 9,454,219 B2* | 9/2016 | Volpe | G06F 1/3296 |
| 10,493,289 B2* | 12/2019 | Volpe | G06F 1/3203 |
| 11,648,412 B2* | 5/2023 | Volpe | G16H 40/63 607/9 |
| 2001/0031991 A1 | 10/2001 | Russial | |
| 2003/0004547 A1 | 1/2003 | Owen et al. | |
| 2003/0032988 A1 | 2/2003 | Fincke | |
| 2003/0095648 A1 | 5/2003 | Kaib et al. | |
| 2005/0131465 A1 | 6/2005 | Freeman et al. | |
| 2005/0144043 A1 | 6/2005 | Holland et al. | |
| 2005/0251213 A1 | 11/2005 | Freeman | |
| 2006/0211934 A1 | 9/2006 | Hassonjee et al. | |
| 2008/0033495 A1 | 2/2008 | Kumar | |
| 2008/0046015 A1 | 2/2008 | Freeman et al. | |
| 2008/0306560 A1 | 12/2008 | Macho et al. | |
| 2008/0306562 A1 | 12/2008 | Donnelly et al. | |
| 2008/0312709 A1 | 12/2008 | Volpe et al. | |
| 2009/0066366 A1 | 3/2009 | Solomon | |
| 2009/0076363 A1 | 3/2009 | Bly et al. | |
| 2009/0076559 A1 | 3/2009 | Libbus et al. | |
| 2009/0118808 A1 | 5/2009 | Belacazar et al. | |
| 2009/0234410 A1 | 9/2009 | Libbus et al. | |
| 2009/0266479 A1 | 10/2009 | Mazar | |
| 2009/0292194 A1 | 11/2009 | Libbus et al. | |
| 2009/0312650 A1 | 12/2009 | Maile et al. | |
| 2010/0010559 A1 | 1/2010 | Zhang et al. | |
| 2010/0052892 A1 | 3/2010 | Allen et al. | |
| 2010/0069735 A1 | 3/2010 | Berkner | |
| 2010/0076533 A1 | 3/2010 | Dar et al. | |
| 2010/0171611 A1 | 7/2010 | Gao et al. | |
| 2010/0298899 A1 | 11/2010 | Donnelly et al. | |
| 2010/0312188 A1 | 12/2010 | Robertson | |
| 2010/0312297 A1 | 12/2010 | Volpe et al. | |
| 2011/0022105 A9 | 1/2011 | Owen et al. | |
| 2011/0034912 A1 | 2/2011 | de Graff et al. | |
| 2011/0066814 A1 | 3/2011 | Narisawa et al. | |
| 2011/0170692 A1 | 7/2011 | Konrad et al. | |
| 2011/0270112 A1 | 11/2011 | Manera | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0146797 A1 | 6/2012 | Oskin et al. | |
| 2012/0150008 A1 | 6/2012 | Kaib et al. | |
| 2012/0158075 A1 | 6/2012 | Kaib et al. | |
| 2012/0283794 A1 | 11/2012 | Kaib et al. | |
| 2012/0289809 A1 | 11/2012 | Kaib et al. | |
| 2012/0293323 A1 | 11/2012 | Kaib et al. | |
| 2012/0302860 A1 | 11/2012 | Volpe et al. | |
| 2013/0013014 A1 | 1/2013 | Donnelly et al. | |
| 2013/0060149 A1 | 3/2013 | Song et al. | |
| 2013/0085538 A1 | 4/2013 | Volpe et al. | |
| 2013/0144355 A1 | 6/2013 | Macho | |
| 2013/0218252 A1 | 8/2013 | Kaib et al. | |
| 2013/0231711 A1 | 9/2013 | Kaib | |
| 2013/0324868 A1 | 12/2013 | Kaib et al. | |
| 2013/0325078 A1 | 12/2013 | Whiting et al. | |
| 2013/0325096 A1 | 12/2013 | Dupelle et al. | |
| 2014/0163334 A1 | 6/2014 | Volpe et al. | |
| 2014/0206974 A1 | 7/2014 | Volpe et al. | |
| 2014/0277243 A1 | 9/2014 | Maskara et al. | |
| 2014/0303680 A1 | 10/2014 | Donnelly et al. | |
| 2014/0324112 A1 | 10/2014 | Macho et al. | |
| 2015/0035654 A1 | 2/2015 | Kaib et al. | |
| 2015/0039039 A1 | 2/2015 | Macho et al. | |
| 2015/0039042 A1 | 2/2015 | Amsler et al. | |
| 2015/0039053 A1 | 2/2015 | Kaib et al. | |

(56) References Cited

U.S. PATENT DOCUMENTS

2015/0080699 A1    3/2015   Kaib et al.
2015/0224330 A1    8/2015   Kaib et al.

FOREIGN PATENT DOCUMENTS

| JP | 2008302225 A | 12/2008 |
|----|--------------|---------|
| JP | 2009510631 A | 3/2009 |
| WO | 8304171 A1 | 12/1983 |
| WO | 1998039061 A2 | 9/1998 |
| WO | 2004078259 A1 | 9/2004 |
| WO | 2009122277 A2 | 10/2009 |
| WO | 2012006524 A1 | 1/2012 |
| WO | 2012006529 A1 | 1/2012 |
| WO | 2013130957 A2 | 9/2013 |
| WO | 2014097035 A1 | 6/2014 |

OTHER PUBLICATIONS http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

Herlihy et al., "The Art of Multiple Processor Programming" Chapter 1, p. 1, Mar. 3, 2008.

International Search Report and Written Opinion from corresponding International Application No. PCT/US2011/043368, dated Nov. 17, 2011.

Wikipedia, Automated External Defibrillator, May 31, 2009, Wikipedia, Section on Mechanism of Operation.

Wikipedia, Multi-Core Processor, Dec. 11, 2009, http://web.archive.org/web/20091211134408/http://en.wikipedia.org/wiki/Multicore_processor#Hardware.

Zoll Medical Corporation, LifeVest Model WCD 3000 Operator's Manual, Pittsburgh, PA. (2012).

\* cited by examiner

SYSTEM AND METHOD FOR CONSERVING POWER IN A MEDICAL DEVICE

CROSS-REFERENCE TO RELATED APPLICATIONS

This application is a continuation of U.S. patent application Ser. No. 16/655,440 (filed 17 Oct. 2019), which is a continuation of U.S. patent application Ser. No. 15/212,993 (filed 18 Jul. 2016; now U.S. Pat. No. 10,493,289), which is a continuation-in-part of U.S. patent application Ser. No. 14/974,794 (filed 18 Dec. 2015; now U.S. Pat. No. 9,454,219), which is a continuation of U.S. patent application Ser. No. 14/531,794 (filed 3 Nov. 2014), which is a continuation of U.S. patent application Ser. No. 12/833,096 (filed 9 Jul. 2010; now U.S. Pat. No. 8,904,214). Each of the aforementioned priority applications is hereby incorporated herein by reference in its entirety for all purposes.

BACKGROUND

Field of Invention

Aspects of the present invention relate to medical devices, and more particularly to apparatus and methods for conserving power in medical devices.

Discussion of Related Art

High performance portable medical devices typically require substantial computer processing power. One factor contributing to the demand for processing power is the large number of peripheral devices supported by many medical devices. These peripheral devices may include display devices such as LCD screens, memory devices such as synchronous dynamic random access memory, secure digital memory, universal sensor data memory and flash memory and interface devices such as universal serial bus, Bluetooth and Ethernet interfaces.

In addition, many portable medical devices perform sophisticated analysis of physiological data gathered from patients. In many instances, this analysis and any treatment initiated as a result of the analysis must be performed quickly, precisely and accurately as a patient's life may depend on it. The complexity and temporal requirements of these processing activities further contributes to the demand for processing power.

Portable medical devices also require that the components used to deliver functionality fit into a small footprint so that the medical device remains portable. In fact, many portable medical devices are required to be small and light enough to be worn by ambulatory patients. To meet these demands, portable medical devices conventionally conform to a design that includes only a single but powerful microprocessor.

SUMMARY OF INVENTION

Aspects and examples disclosed herein manifest an appreciation that the processing power required by portable medical devices equates to a significant load on the batteries used to power these devices. This, in turn, causes the battery runtime to decrease and the frequency with which batteries need recharging to increase. Consequently, the useful lifespan of the batteries is shortened. Additionally, other aspects and examples disclosed herein manifest an appreciation that, for some medical devices, conventional real time operating systems (RTOSs) lack the ability to execute instructions with the temporal precision required to effectively implement treatment methods.

For instance, some examples disclosed herein conserve battery power by implementing a processor architecture that includes a plurality of processors. At least one of these processors is a dual core processor configured to determine if a condition in the patient exists that requires a treatment sequence, and a high voltage processor in communication with therapy electrodes to initiate a treatment sequence.

In one embodiment, a therapeutic medical device is provided. The therapeutic medical device includes at least one sensor interface configured to receive physiologic data descriptive of a patient; at least one therapy delivery device; a first processor coupled to the at least one therapy delivery device and configured to control the at least one therapy delivery device to deliver treatment to the patient in response to receiving a signal; and a second processor distinct from the first processor, the second processor being coupled to the at least one sensor interface and being configured to receive the physiologic data via the at least one sensor interface, to process the physiologic data to detect a condition of the patient, and to transmit, in response to detecting the condition, the signal to the first processor.

In the therapeutic medical device, the second processor may include a dual core processor. The dual core processor may include an Advanced RISC Machine (ARM) core and a digital signal processing (DSP) core. The ARM core may be configured to receive the physiologic data from the DSP core and to detect the condition, and the DSP core may be configured to process the physiologic data to identify a time to deliver the treatment based upon the physiologic data. The treatment may include at least one electric pulse.

The therapeutic medical device may further include at least one physiologic sensor and a belt node processor coupled to the at least one physiologic sensor and the at least one sensor interface and configured to convert the physiologic signal to the physiologic data and to transmit the physiological data to the second processor via the at least one sensor interface. The belt node processor may be configured to control deployment of a therapeutic gel by the at least one therapy delivery device. The first processor and the second processor may be configured to communicate using at least one of a UART protocol, a wireless communication protocol, a serial communication protocol, a CAN protocol, a USB protocol or a GPIO protocol and the second processor and the physiologic sensor communicate over a CAN bus interface.

In the therapeutic medical device, the second processor may be configured to receive incoming CAN packets containing the physiologic data; analyze the physiologic data; detect the condition; and control a treatment sequence including transmission of the signal to the first processor. The therapeutic medical device may further include a user interface comprising at least one of a display screen and a touchscreen. The user interface may be coupled to the second processor and may further include a response button configured to provide an input to the second processor, the input indicating a delay of initiation of the treatment.

In another embodiment, a method is provided. The method includes acts of receiving, by a dual core processor, physiologic data descriptive of a patient; analyzing, by the dual core processor, the physiologic data to determine that a treatment sequence is necessary; transmitting, by the dual core processor, a signal to a high voltage processor, the signal indicating to the high voltage processor that the treatment sequence is necessary; controlling, by the high voltage processor, a therapy delivery device in response to receiving the signal from the dual core processor; and transmitting, by the dual core processor, a synchronization control signal to the high voltage processor to synchronize the treatment sequence with a condition of the patient.

The method may further include acts of receiving an input from a response button and delaying the treatment sequence. The method may further include acts of capturing the physiologic data by a belt node processor in communication with a DSP core of the dual core processor and controlling, by the belt node processor, deployment of gel to a therapeutic electrode. The method may further include acts of receiving, by an ARM core of the dual core processor, incoming CAN packets containing the physiologic data; analyzing, by the ARM core, the physiological data; determining, by the ARM core, that the treatment sequence is necessary; and executing, by the ARM core, the treatment sequence.

In another embodiment, a therapeutic medical device is provided. The therapeutic medical device includes at least one therapy delivery device; a high voltage processor coupled to the therapy delivery device and configured to control the therapy delivery device to deliver a treatment in response to receiving a signal; and a dual core processor, distinct from the high voltage processor, coupled to the high voltage processor and configured to receive physiologic data, to process the physiologic data to detect a condition of a patient, and to transmit, in response to detecting the condition of the patient, the signal to the high voltage processor.

In the therapeutic medical device, the dual core processor may include an Advanced RISC Machine (ARM) core and a digital signal processor (DSP) core. The ARM core may be configured to receive the physiologic data from the DSP core and to detect the condition, and the DSP core may be configured to process the physiologic data to identify a time to deliver the treatment based upon the physiologic data. The dual core processor may be embedded within a portable treatment controller of a therapeutic medical device. The portable treatment controller may be coupled to at least one physiological sensor and at least one therapy delivery device. The therapeutic medical device may further include a belt node processor configured to capture the physiological data from the at least one physiological sensor and to provide the physiological data to the dual core processor. The therapeutic medical device may further include a communication interface comprising a short range wireless communication interface. The therapeutic medical device may further include a user interface, the user interface comprising a display screen and a touchscreen. The therapeutic medical device may further include a response button configured to provide an input to the dual core processor, the input indicating a delay of initiation of the treatment sequence.

In another embodiment, a therapeutic medical device is provided. The therapeutic medical device includes at least one sensor interface configured to receive physiologic data descriptive of a patient; at least one therapy delivery device; a first processor coupled to the at least one therapy delivery device and configured to control the at least one therapy delivery device to deliver treatment to the patient; and a second processor distinct from the first processor, the second processor being coupled to the at least one sensor interface and being configured to receive the physiologic data via the at least one sensor interface, to process the physiologic data to detect a condition of the patient, and to cause the first processor to deliver the treatment in response to detecting the condition. The treatment may include at least one electric pulse.

The therapeutic medical device may further include a shared memory in communication with at least one of the first processor and the second processor. The shared memory may be configured to store at least a portion of the physiologic data descriptive of the patient. The first processor may be configured to analyze the portion of the physiologic data in the shared memory and determine, based on the portion of the physiologic data, whether a critical event has occurred. The first processor and the second processor may communicate using at least one of a UART protocol, a wireless communication protocol, a serial communication protocol, a CAN protocol, a USB protocol or a GPIO protocol and the second processor and the physiologic sensor communicate over a CAN bus interface.

In the therapeutic medical device, the second processor may be configured to receive the physiologic data at least in part by receiving incoming packets containing the physiologic data; process the physiologic data at least in part by analyzing the incoming packets containing the physiologic data; and cause the first processor to deliver the treatment at least in part by transmitting a signal to the first processor. The first processor may be configured to control the at least one therapy delivery device to deliver treatment according to a default timeline. The second processor may be configured to adjust the default timeline. The second processor may be configured to adjust the default timeline to synchronize the treatment based on the physiologic data descriptive of the patient.

In the therapeutic medical device, the physiologic data descriptive of the patient may include electrocardiogram (ECG) data. The second processor may be configured to adjust the default timeline to synchronize the treatment with an R-wave of the ECG data.

In the therapeutic medical device, the second processor may include a dual core processor. The dual core processor may include an application core and a signal processing core. The application core may be configured to receive the physiologic data from the signal processing core and to detect the condition. The signal processing core may be configured to process the physiologic data to identify a time to deliver the treatment based upon the physiologic data.

The therapeutic medical device may further include at least one physiologic sensor and a belt node processor coupled to the at least one physiologic sensor and the at least one sensor interface and configured to convert the physiologic signal to the physiologic data and to transmit the physiological data to the second processor via the at least one sensor interface. The belt node processor may be configured to control deployment of a therapeutic gel by the at least one therapy delivery device.

The therapeutic medical device may further include a user interface comprising at least one of a display screen and a touchscreen. The user interface may be coupled to the second processor and may further include a response button configured to provide an input to the second processor that causes a delay of initiation of the treatment.

In another embodiment, a method of treatment for a patient using a therapeutic medical device comprising a first processor and a second processor distinct from the first processor is provided. The method includes acts of receiving, by the first processor via at least one sensor interface, physiologic data descriptive of a patient; processing, by the first processor, the physiologic data to detect a condition of the patient; and causing, by the first processor in response to detecting the condition, the second processor to control at least one therapy delivery device to deliver treatment to the patient.

In the method, the act of causing the second processor to control the at least one therapy delivery device may include an act of causing the second processor to control the at least one therapy delivery device to deliver at least one electric pulse. In the method, the act of receiving the physiologic data may include an act of receiving incoming packets containing the physiologic data, the act of processing the physiologic data may include an act of analyzing the incoming packets, and the act of causing the second processor to control the at least one therapy delivery device may include an act of transmitting a signal to the second processor to cause the second processor to deliver the treatment.

According to one example, a therapeutic medical device is disclosed. The therapeutic medical device comprises at least one sensor interface configured to receive physiologic data descriptive of a patient and at least one therapy delivery device. The therapeutic medical device comprises a first processor coupled to the at least one therapy delivery device and to a control interface and configured to control the at least one therapy delivery device to deliver treatment to the patient in response to receiving a signal and a second processor distinct from the first processor, the second processor being coupled to the at least one sensor interface and being configured to receive the physiologic data via the at least one sensor interface, to process the physiologic data to detect a condition of the patient, and to transmit, in response to detecting the condition, the signal to the first processor. The second processor includes a dual core processor that, for example, comprises an Advanced RISC Machine (ARM) core and a digital signal processor (DSP) core. The ARM core is configured to receive the physiologic data from the DSP core and to detect the condition, and the DSP core is configured to process the physiologic data to identify a time to deliver the treatment based upon the physiologic data. The treatment includes at least one electric pulse. The therapeutic medical device comprises at least one physiologic sensor and a belt node processor coupled to the at least one physiologic sensor and the at least one sensor interface and configured to convert the physiologic signal to the physiologic data, and to transmit the physiological data to the DSP core via the at least one sensor interface. The belt node processor is configured to control deployment of a therapeutic gel to the at least one therapy delivery device. The first processor and the dual core processor communicate using a UART protocol, a wireless communication protocol (e.g., WiFi®), a serial communication protocol, a CAN protocol, a USB protocol or a GPIO protocol, wherein the dual core processor and the physiologic sensor communicate over a CAN bus interface. The ARM core is configured to receive incoming CAN packets containing the physiologic data, analyze the physiologic data, detect the condition, and control a treatment sequence including transmission of the signal to the first processor. The therapeutic medical device comprises a user interface, the user interface comprising a display screen and a touchscreen. The user interface is coupled to the ARM core and further comprises a response button configured to provide an input to the ARM core, the input indicating a delay of initiation of the treatment.

In one example, a method comprises receiving, by a dual core processor, physiologic data, analyzing, by the dual core processor, the physiologic data to determine that a treatment sequence is necessary, transmitting, by the dual core processor, a signal to a high voltage processor, the signal indicating to the high voltage processor that the treatment sequence is necessary, controlling, by the high voltage processor, a therapy delivery device in response to receiving the signal from the dual core processor, and transmitting, by the dual core processor, a synchronization control signal to the high voltage processor to synchronize the treatment. The method can further comprise receiving an input from a response button and delaying the treatment sequence. The method can further comprise capturing the physiologic data by a belt node processor in communication with a DSP core of the dual core processor, and controlling, by the belt node processor, deployment of gel to a therapeutic electrode. The method can further comprise receiving, by an ARM core of the dual core processor, incoming CAN packets containing the physiologic data, analyzing, by the ARM core, the physiological data, determining, by the ARM core, that the treatment sequence is necessary, and executing, by the ARM core, the treatment sequence.

In one example, a therapeutic medical device comprises at least one therapy delivery device, a high voltage processor and a dual core processor. The high voltage processor is coupled to the therapy delivery device and configured to control the therapy delivery device to deliver a treatment in response to receiving a signal. The dual core processor is distinct from the high voltage processor and comprises an Advanced RISC Machine (ARM) core and a digital signal processor (DSP) core, the dual core processor coupled to the high voltage processor and configured to receive physiologic data, to process the physiologic data to detect a condition of a patient, and to transmit, in response to detecting the condition of the patient, the signal to the high voltage processor. The dual core processor can be embedded within a portable treatment controller of a therapeutic medical device, the portable treatment controller coupled to at least one physiological sensor and at least one therapy delivery device. The therapeutic medical device can also comprise a belt node processor configured to capture the physiological data from the at least one physiological sensor and provide the physiological data to the DSP core of the dual core processor. The therapeutic medical device can further comprise a user interface, the user interface comprising a display screen and a touchscreen. The therapeutic medical device can further comprise a response button configured to provide an input to the ARM core, the input indicating a delay of initiation of the treatment sequence. The ARM core is configured to receive the physiologic data from the DSP core and to detect the condition, and the DSP core is configured to process the physiologic data to identify a time to deliver the treatment based upon the physiologic data.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example. Furthermore, in the event of inconsistent usages of terms between this document and documents incorporate herein by reference, the term usage in the incorporated references is supplementary to that of this document; for irreconcilable inconsistencies, the term usage in this document controls.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of the invention. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

DETAILED DESCRIPTION

Figure 1:
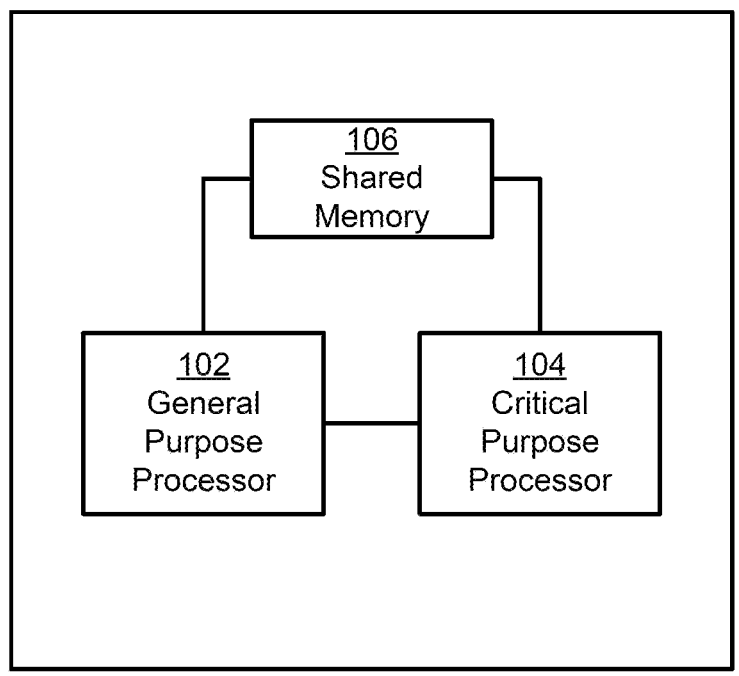
FIG. 1 is a functional block diagram of one example of a power conserving processor arrangement.

Aspects and examples relate to apparatus and processes for selectively executing instructions on particular processors within a processor arrangement. The manner in which the instructions are executed conserves electrical energy and isolates particular functionality to particular components. For instance, methods and apparatus in accord with some examples include a medical device having a critical purpose processor that is configured to execute one or more critical functions and a general purpose processor that is configured to execute the remainder of the functions of the medical device. In these examples, the critical purpose processor generally remains active while the general purpose processor generally remains inactive. This arrangement of processors results in lower power consumption by the medical device than would an arrangement including only the general purpose processor. Lower power consumption, in turn, results in decreased operating temperature which extends the life and reliability of the medical device.

In addition, this arrangement of processors isolates execution of the critical functions to a particular set of components. In this way, the processor arrangement protects the ability of the medical device to reliably, precisely and effectively execute its critical functions without interference or instability caused by execution of or change to the non-critical functions of the device. Moreover, by including a general purpose processor that executes an RTOS, this arrangement provides a rich computing platform with standard system services such as file system management and communications for the remainder of the functions of the medical device.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Power Conserving Processor Arrangement

Various examples disclosed herein conserve electrical power by harnessing multiple processors that use differing amounts of power during operation. FIG. 1 illustrates a power conserving processor arrangement 100 that is specially configured to utilize less power than a conventional, comparable single processor architecture while providing at least the same level of processing functionality as the single processor architecture. The power conserving processor arrangement 100 includes a general purpose processor 102, a critical purpose processor 104 and shared memory 106. As shown, each of these components is coupled to the other two. Both of the processors 102 and 104 can perform a series of instructions that result in manipulated data which can be stored in and retrieved from the shared memory 106. In addition, the critical purpose processor 104 can actively operate using less electrical power than the general purpose processor 102. By taking advantage of this feature, the power conserving processor arrangement 100 saves energy by employing the critical purpose processor 104 to execute instructions that would normally be executed on the general purpose processor 102 under a conventional design.

Some exemplary devices also employ the power conserving processor arrangement 100 to isolate execution of functions that are critical to the purpose of the device. In these exemplary devices, critical functions are performed by the critical purpose processor 104. Critical functions are a well defined set of limited or essential functions that the medical device employing the power conserving processor arrangement 100 is designed to provide. Particular examples of critical functions are discussed in further detail below. In addition, according to these examples, non-critical functions are performed by the general purpose processor 102. This segmentation of instruction execution provides several benefits which are discussed further below.

According to some examples, the general purpose processor 102 is configurable to operate in one of a plurality of service states that each consume differing, predetermined levels of electrical power. Moreover, in these examples, the general purpose processor 102 is configured to operate at a predefined performance level within each service state. The particular number of service states and the characteristics of the level of performance associated with each service state vary by the manufacturer or model of the processor. However, many processors conform to electrical power management standards such as the "Advanced Configuration and Power Interface Specification," (ACPI) Revision 4.0a which was published at www.acpi.info on Apr. 5, 2010. The ACPI defines processor service states and the characteristics of the level of performance associated with these service states. For example, processors complying with the ACPI may assume various power, performance and throttling states. Each of these states is associated with an amount of electrical power required to support the service state and a guaranteed level of processor performance. The aspects of processor performance that may be manipulated by various service states include, among others, the clock rate of the processor and the latency time required for the processor to assume a different service state.

In some examples, the service states that the general purpose processor 102 can assume include an active service state or one of several reduced service states. While operating in the active service state, the general purpose processor 102 can operate at or near peak performance. Thus, while in the active service state, the general purpose processor 102 can execute instructions at, or near, the maximum clock rate, maintain coherent processor caches and shift into other service states with minimal, or near minimal, latency. An example of an active service state includes the C0 power state, as defined in ACPI, when combined with a P0 performance state and with or without throttling.

When operating in reduced service states, the general purpose processor 102 operates at less than peak performance. Examples of reduced service states include the C0 power state, when combined with a performance state other than P0, and any of the processor sleeping states, such as the C1 and C2 power states. The processor functionality available under these service states varies according the particular reduced service state assumed.

For example, when the general purpose processor 102 is placed in a C0 state combined with a non-P0 state, the general purpose processor 102 can execute instructions and maintain cache coherency but does so at a rate less than the maximum clock rate. Also, when the general purpose processor 102 is placed in a processor sleeping state, the general purpose processor 102 cannot execute instructions and the processor caches are flushed and invalidated. In addition, while operating in a processor sleeping state, the general purpose processor 102 may (depending on the particular processor sleeping state) require more latency time to shift into another service state. However, when in these states, the general purpose processor 102 consumes less electrical power than when in an active service state.

According to some examples, the critical purpose processor 104 is also configurable to operate in a variety of service states. These service states include at least one service state that enables the critical purpose processor 104 to execute instructions using significantly less power than would the general purpose processor 102. In addition, these service states include at least one service state that provides a performance level required for the critical purpose processor 104 to carry out a set of critical functions. In some of these examples, the critical functions have strict timing requirements that are better met by a dedicated execution environment, such as the execution environment provided by the critical purpose processor 104. For instance, some critical functions may require low jitter and response times ranging from approximately 10 milliseconds down to and including less than approximately 10 microseconds. According to these examples, the critical purpose processor 104, by executing the critical functions, allows the general purpose processor 102 to execute processes with less stringent requirements.

In some examples, the general purpose processor 102 is configured to provide an interface through which the general purpose processor 102 can receive, process and respond to service requests. These service requests may include information indicating the source of the request, the requested functions to be performed, service states to be assumed and maximum durations of active processing activity. According to these examples, the general purpose processor 102 is configured take a variety of actions in response to a service request. These actions may include verifying the source of the request, and upon proper verification of the source, assuming the requested service state, performing the requested functions and entering a reduced service state upon reaching the specified maximum duration of active execution or upon expiration of a predetermined time period.

Also, according to these examples, the critical purpose processor 104 includes a power management component that is configured to issue a service request to the general purpose processor 102 when the critical purpose processor 104 encounters an event. Events that cause the power management component to issue a service request may include any event that requires processing by the general purpose processor 102. More specifically, in some of these examples, the power management component is configured to issue a service request upon detection that the shared memory 106 is full, that a critical event has occurred or that a predetermined period of time since the general purpose processor 102 was active has transpired. A critical event may include any event related to execution of critical functionality.

In addition, in some examples, the predetermined period of time is configurable. More particularly, in at least one of these examples, the power management component is configured to issue service requests that cause the general purpose processor 102 to activate every 5 minutes and stay active for a duration of 5 seconds. In other examples, the power management component is configured for execution on a separate programmable logic device (PLD) rather than on the critical purpose processor 104.

Also, some examples implement a watchdog component that monitors the operations of the general purpose processor 102 and the critical purpose processor 104. According to these examples, while both processors are operating normally, each processor transmits a special message (referred to as a "heartbeat message") to the watchdog component at a predetermined interval specific to the processor. For instance, the predetermined interval at which the general purpose processor 102 transmits messages to the watchdog component may be 5 minutes, while the predetermined interval at which the critical purpose processor 104 transmits messages may be 1 second. If the watchdog component does not receive the messages according to the predetermined intervals, the watchdog component resets the device. In at least some examples, the watchdog component is implemented as a software process on a PLD that is separate from the general purpose processor 102 and the critical purpose processor 104.

Further, in some examples, the length of the predetermined interval is configurable or depends on previous detection of a critical event. In at least one example, the predetermined interval associated with the general purpose processor 102 is 5 minutes unless a critical event has been detected. In that instance, however, the critical purpose processor 104 temporarily sets the predetermined interval associated with the general purpose processor 102 to 5 seconds to decrease any potential latency associated with the general purpose processor 102 and the device overall. Further, in these examples, after performing any processing associated with the critical event, the general purpose processor 102 sets the predetermined interval associated with itself back to 5 minutes prior to entering a reduced service state.

According to a variety of examples, the processors 102 and 104 are commercially available processors such as processors manufactured by Texas Instruments, Intel, AMD, Sun, IBM, Motorola, Freescale and ARM Holdings. However, the processors 102 and 104 may be any type of processor, multiprocessor or controller, whether commercially available or specially manufactured. In some examples, the critical purpose processor 104 is a digital signal processor, a field-programmable gate array or a PLD. In at least one particular example, the general purpose processor 102 is an Intel® PXA270 and the critical purpose processor 104 is a Freescale™ DSP56311.

In addition, in several examples the general purpose processor 102 is configured to execute a conventional RTOS, such as RTLinux. In these examples, the RTOS may provide platform services to application software. These platform services may include inter-process and network communication, file system management and standard database manipulation. However, one of many operating systems may be used, and examples are not limited to any particular operating system or operating system characteristic. For instance, in some examples, the general purpose processor 102 may be configured to execute a non real time operating system, such as BSD or GNU/Linux.

In the example illustrated in FIG. 1, the shared memory 106 is configured to store data during operation of the power conserving processor arrangement 100. In some examples, the shared memory 106 includes a relatively high performance, volatile, random access memory such as dynamic random access memory (DRAM), static memory (SRAM) or synchronous DRAM. However, the shared memory 106 may include any device for storing data, such as a non-volatile memory, with sufficient throughput and storage capacity to support the functions described herein. In the example of FIG. 1, the shared memory 106 has a storage capacity of 1 megabyte and is coupled to both processors 102 and 104. Thus in some examples, the shared memory 106 may include hardware or software configured to enable concurrent access to stored data. In at least one example, the shared memory 106 includes dual port RAM. While in other examples, the shared memory 106 includes a PLD coupled to a single port synchronous DRAM. In these examples, the PLD provides an interface that services concurrent memory requests from the processors 102 and 104.

According to some examples, the general purpose processor 102 swaps between a critical purpose operating system and a general purpose operating system and exploits differences between the operating power requirements of each operating system to conserve power used by the device. In these examples, each of the operating systems operates a subset of the overall peripherals available to the general purpose processor 102. The particular peripherals operated by either operating system are based on the functionality executed within each operating system. Thus, the critical purpose operating system may operate different peripherals than the general purpose operating system. Examples of these peripherals include any hardware that interacts with a processor. Thus, exemplary peripherals include memory, UARTs, display controllers, audio controllers, USB controllers and wireless or wired network interface controllers, among others.

Also, according to these examples, a device including the general purpose processor 102 configured to swap operating systems conserves power because while either operating system is running, a power management component places the peripherals that are operated by the dormant operating system into a reduced service state. The particular service state into which the power management component places each peripheral depends on the sophistication of each peripheral. For instance, in some examples, the power management component can simply discontinue supply of power to peripherals with insufficient power state management functionality to be managed in another way, such as some types of memory. While in other examples, the power management component can issue commands to enter reduced service states to peripherals exposing power state management interfaces, such as certain models of UARTs.

Figure 2:
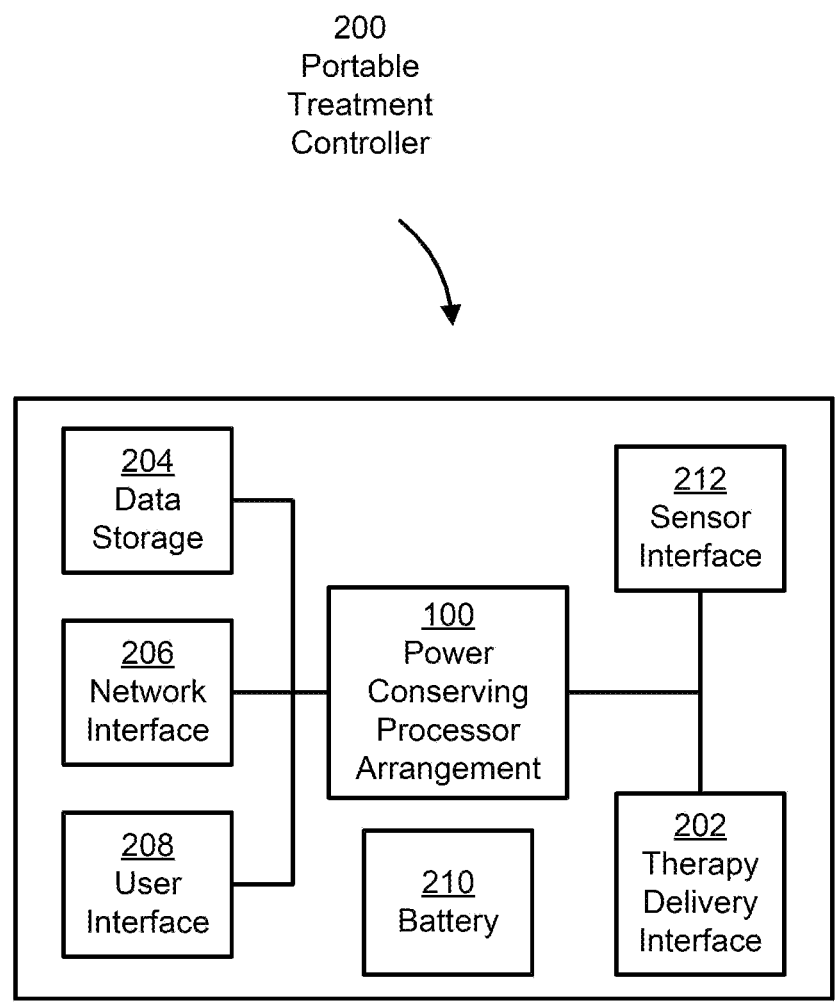
FIG. 2 is a functional block diagram of one example of a portable treatment controller.
Figure 3:
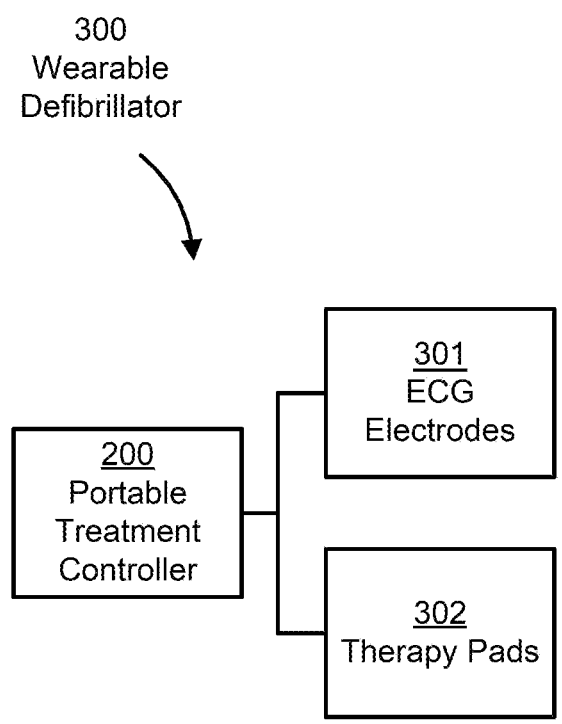
FIG. 3 is a functional block diagram of one example of a wearable defibrillator.

The power conserving processor arrangement 100 has a variety of potential applications and is well suited to devices that must perform a critical set of functions in an environment with scarce resources. Examples of such devices include critical care medical devices, such as a wearable external defibrillator. The power conserving processor arrangement 100 may also be leveraged to isolate particular components of a device when it is advantageous to do so, for example, to allow government regulated components of a device to remain unchanged while introducing new functionality to a device via other components. FIG. 2 and FIG. 3 illustrate examples of devices that utilize the power conserving processor arrangement 100. In addition, the power conserving processor arrangement 100 may be included within a wearable medical treatment device as described in commonly owned U.S. Patent Application entitled "Wearable Medical Treatment Device," filed on even date herewith, which is incorporated by reference herein in its entirety.

Portable Treatment Controller

FIG. 2 illustrates a portable treatment controller 200 that is configured to perform the critical functions of monitoring physiological information for abnormalities and initiating treatment of detected abnormalities. As shown, the portable treatment controller 200 includes the power conserving processor arrangement 100, a sensor interface 212, a therapy delivery interface 202, data storage 204, a communication network interface 206, a user interface 208 and a battery 210. In this illustrated example, the battery 210 is a rechargeable 3 cell 2200 mAh lithium ion battery pack that provides electrical power to the other device components with a minimum 24 hour runtime between charges. The sensor interface 212 and the therapy delivery interface 202 are coupled to the power conserving processor arrangement 100 and more particularly to the critical purpose processor 104. The sensor interface 212 and the therapy delivery interface 202 are coupled to the critical purpose processor 104 and the critical purpose processor 104 is configured to perform the critical functions of the portable treatment controller 200 using interfaces 202 and 212. As is discussed further below, in some examples these functions include functions requiring a real time processing. For instance, within the context of a wearable defibrillator such as the wearable defibrillator discussed below with regard to FIG. 3 below, these critical functions may include charging the capacitors to a particular voltage, digital sampling and analysis of electrocardiogram (ECG) information and generation of the delivered energy waveform.

Analogously, the data storage 204, the network interface 206 and the user interface 208 are also coupled to the power conserving processor arrangement 100, and more particularly to the general purpose processor 102, and the general purpose processor 102 is configured to perform the non-critical functions using these components. In some examples, these non-critical functions include functions that do not require real time processing. Under the design illustrated in FIG. 2, the portable treatment controller 200 can perform both critical and non-critical functions while consuming less energy than a conventional, single processor device having the same functionality. In addition, the portable treatment controller 200 shown in FIG. 2 prevents disruption of critical functions from hardware and software faults that may occur during execution of non-critical functions.

In the example shown, the data storage 204 includes a computer readable and writeable nonvolatile data storage medium configured to store non-transitory instructions and other data. The instructions may include executable programs or other code that can be executed by either the general purpose processor 102 or the critical purpose processor 104. The data storage 204 also may include information that is recorded, on or in, the medium, and this information may be processed by the processor 102 or 104 during execution of instructions. More specifically, the information may be stored in one or more data structures specifically configured to conserve storage space or increase data exchange performance. The instructions may be persistently stored as encoded signals, and the instructions may cause the processors 102 or 104 to perform any of the functions described herein. The medium may, for example, be optical disk, magnetic disk or flash memory, among others and may be permanently affixed to, or removable from, the portable treatment controller 200.

According to several examples, the general purpose processor 102 is configured to cause data to be read from the nonvolatile recording medium into another memory, such as the shared memory 106 described above with reference to FIG. 1, that allows for access to the data by either of the processors 102 or 104. The processors 102 or 104 can manipulate the data within the shared memory 106, and the general purpose processor 102 can copy the data to the storage medium associated with the data storage 204 after processing is completed. A variety of components may manage data movement between the data storage 204 and the shared memory 106 and examples are not limited to particular data management components. Further, examples are not limited to a particular memory, memory system or data storage system.

As shown in FIG. 2, the portable treatment controller 200 includes several system interface components 202, 206 and 212. Each of these system interface components is configured to exchange, i.e. send or receive, data with specialized devices that may be located within the portable treatment controller 200 or elsewhere. The components used by the interfaces 202, 206 and 212 may include hardware components, software components or a combination of both. In the instance of each interface, these components physically and logically couple the portable treatment controller 200 to one or more specialized devices. This physical and logical coupling enables the portable treatment controller 200 to both communicate with and, in some instances, control the operation of specialized devices. As discussed further below, these specialized devices may include physiological sensors, therapy delivery devices and computer networking devices.

According to various examples, the hardware and software components of the interfaces 202, 206 and 212 employ a variety of coupling and communication techniques. In some examples, the interfaces 202, 206 and 212 use leads, cables or other wired connectors as conduits to exchange data between the portable treatment controller 200 and specialized devices. In other examples, the interfaces 202, 206 and 212 communicate with specialized devices using wireless technologies such as radio frequency or infrared technology. The software components included in the interfaces 202, 206 and 212 enable the power conserving processor arrangement 100 to communicate with specialized devices. These software components may include elements such as objects, executable code and populated data structures. Together, these software components provide software interfaces through which the power conserving processor arrangement 100 can exchange information with specialized devices. Moreover, in at least some examples where one or more specialized devices communicate using analog signals, the interfaces 202, 206 and 212 further include components configured to convert analog information into digital information, and vice versa, to enable the power conserving processor arrangement 100 to communicate with specialized devices.

As discussed above, the system interface components 202, 206 and 212 shown in the example of FIG. 2 support different types of specialized devices. For instance, the components of the sensor interface 212 couple the power conserving processor arrangement 100, and, in some examples, the critical purpose processor 104, to one or more physiological sensors such as body temperature sensors, respiration monitors and dry capacitive electrocardiographic (ECG) electrodes. Additionally, in some examples, the components of the sensor interface 212 couple the general purpose processor 102 to one or more physiological sensors. In these examples, the one or more physiological sensors may include sensors with a relatively low sampling rate, such as wireless sensors.

In some examples, the sensor interface 212 includes a falloff detection component configured to sense a lack of proper coupling between these physiological sensors and a patient. In these examples, the critical purpose processor 104 is configured to record this critical event in the shared memory 106 and issue a service request to the general purpose processor 102. Further, in these examples, the general purpose processor 102 is configured to notify a user of the decoupled sensor via the user interface 208.

The components of the therapy delivery interface 202 couple one or more therapy delivery devices, such as capacitors and defibrillator electrodes, to the critical purpose processor 104. In addition, the components of the network interface 206 couple the general purpose processor 102 to a computer network via a networking device, such as a bridge, router or hub. According to a variety of examples, the network interface 206 supports a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the portable treatment controller 200 can transmit data via the network interface 206 using a variety of security measures including, for example, TLS, SSL or VPN. In other examples, the network interface 206 includes both a physical interface configured for wireless communication and a physical interface configured for wired communication.

Thus, the various system interfaces incorporated in the portable treatment controller 200 allow the device to interoperate with a wide variety of devices in various contexts. For instance, some examples of the portable treatment controller 200 are configured to perform a process of sending critical events and data to a centralized server via the network interface 206. An illustration of a process in accord with these examples is disclosed in U.S. Pat. No. 6,681,003, entitled "DATA COLLECTION AND SYSTEM MANAGEMENT FOR PATIENT-WORN MEDICAL DEVICES" and issued on Jan. 20, 2004 which is hereby incorporated by reference in its entirety.

The user interface 208 shown in FIG. 2 includes a combination of hardware and software components that allow the portable treatment controller 200 to communicate with an external entity, such as a user. These components are configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens and speakers.

In some examples, the portable treatment controller 200 includes additional components configured to enable the portable treatment controller 200 to recover from operational failure. For instance, as discussed above according to one example, the portable treatment controller 200 includes a watchdog component configured to perform a restart of the portable treatment controller 200. In this example, either the general purpose processor 102 or the critical purpose processor 104 can force a restart of the portable treatment controller 200 via the watchdog component, should either processor encounter an unrecoverable hardware or software fault.

The particular abnormalities treatable by the portable treatment controller 200 vary based on the type of physiological information collected via the sensor interface 212 and the therapies that can be initiated via the therapy delivery interface 202. For instance, according to some examples, the sensor interface 212 includes components configured to receive ECG data. Also, in these examples, the therapy delivery interface 202 includes components configured to deliver a therapeutic shock to the heart of a patient in the event that the ECG data indicates a cardiac dysrhythmia. A particular example of the portable treatment controller 200 that is included in a wearable defibrillator is discussed below with reference to FIG. 3.

Wearable Defibrillator

FIG. 3 is a functional block diagram of a wearable defibrillator 300 that is configured to implement the critical functions of monitoring an ambulatory patient's ECG information and, when needed, administering a therapeutic shock to the patent. Such a wearable defibrillator is ideally suited to take advantage of the unique capabilities afforded by the portable treatment controller 200. For example, wearable defibrillators, such as the LifeVest® wearable defibrillator available from ZOLL® Corporation, are typically worn nearly continuously for two to three months at a time. During the period of time in which they are worn, the wearable defibrillator needs to continuously monitor the vital signs of the patient, to be user friendly and accessible, to be as lightweight, comfortable, and portable as possible, and to be capable of delivering one or more life-saving therapeutic shocks when needed. Given the substantial amount of power that needs to be delivered during each therapeutic shock, it is imperative that power consumption during normal patient monitoring and operation be reduced to an absolute minimum.

As illustrated, the wearable defibrillator 300 includes the portable treatment controller 200, ECG electrodes 301 and therapy pads 302. The ECG electrodes 301 are coupled to the portable treatment controller, and more particularly to the critical purpose processor 104, via the sensor interface 212. Similarly, the therapy pads 302 are coupled to the portable treatment controller 200, and more specifically to the critical purpose processor 104, via the therapy delivery interface 202.

When utilized in the example of the wearable defibrillator 300, the components of the portable treatment controller 200 are further configured to support the critical functions of the wearable defibrillator 300. More specifically, according to this example, the battery 210 has sufficient capacity to administer one or more therapeutic shocks and the therapy delivery interface 202 has wiring suitable to carry the load to the therapeutic electrodes. Moreover, in the example shown, the battery 210 has sufficient capacity to deliver up to 5 or more therapeutic shocks, even at battery runtime expiration. As previously noted, the power delivered by a therapeutic shock of the wearable defibrillator 300 is substantial, for example approximately 150 Joules. Despite the large amount of power needed to deliver a therapeutic shock and the small footprint of the device itself, the wearable defibrillator 300 can charge capacitors within 20 seconds, notify the patient that a therapeutic shock is imminent, wait for a period (e.g. 25 seconds) to allow a patient to prevent treatment, and if appropriate, deliver the therapeutic shock within total elapsed time of 40 to 45 seconds from detection of a condition treatment without disruption to its data processing and analysis capabilities. This quick charge capability is important because the efficacy of the therapeutic shock decreases significantly when delivered over 1 minute after indication of an abnormal rhythm that should be treated with a therapeutic shock.

Continuing this example, the critical purpose processor 104 is configured to receive ECG information from the ECG electrodes 301, detect abnormal heart rhythms based on the information received from the ECG electrodes 301, charge capacitors coupled to the therapy pads 302 and administer a therapeutic shock to the patient, unless a user intervenes within a predetermined period of time via the user interface 208. In at least one example, the predetermined period of time in which a user may intervene does not end until actual delivery of the therapeutic shock. An example of the methods used to detect abnormal heart rhythms can be found in U.S. Pat. No. 5,944,669, entitled "APPARATUS AND METHOD FOR SENSING CARDIAC FUNCTION" and issued on Aug. 31, 1999 which is hereby incorporated by reference in its entirety. Additionally, an example of the general features of a wearable defibrillator can be found in U.S. Pat. No. 6,280,461, entitled "PATIENT-WORN ENERGY DELIVERY APPARATUS" and issued on Aug. 28, 2001 which is hereby incorporated by reference in its entirety.

In another example of the wearable defibrillator 300, the general purpose processor 102 is configured to perform several non-critical functions. These non-critical functions may leverage the robust computing platform provided by the general purpose processor 102 (in combination with an RTOS) without disrupting the critical functions of the device. Some examples of these non-critical functions include notifying emergency personnel of the location of a patient who just received a therapeutic shock via the network interface 206, providing users of the device with the historical physiological data of the wearer of the device via the user interface 208 and notifying the device manufacturer of potential performance issues within the device that may require repair to or replacement of the device via the network interface 206. Moreover, these non-critical functions include maintaining a history of data and events by storing this information in the data storage 204, communicating with the user via the user interface 208 and reporting data and events via the network interface 206. Example processes used to conserve energy while processing critical events and maintaining the history of critical data are discussed further below with regard to FIGS. 4, 5 and 6. In addition, other non-critical functions may perform additional operations on the history of critical data. For instance, in one example, a non-critical function analyzes the history of critical data to predict worsening heart failure or an increased risk of sudden cardiac death.

In other examples, a wearable defibrillator includes additional devices, features and functions that, when integrated with the computing platform based on the power conserving processor arrangement 100, allow the wearable defibrillator to adapt, over extended periods of time, to the individual needs of each patient. One such example is disclosed with reference FIG. 1 of co-pending U.S. patent application Ser. No. 12/002,469, entitled "WEARABLE MEDICAL TREATMENT DEVICE WITH MOTION/POSITION DETECTION" and filed on Dec. 17, 2007 which is hereby incorporated by reference in its entirety. This example includes additional sensors, such as motion sensors, to provide additional functionality and is illustrated herein with reference to FIG. 3A.

Figure 3A:
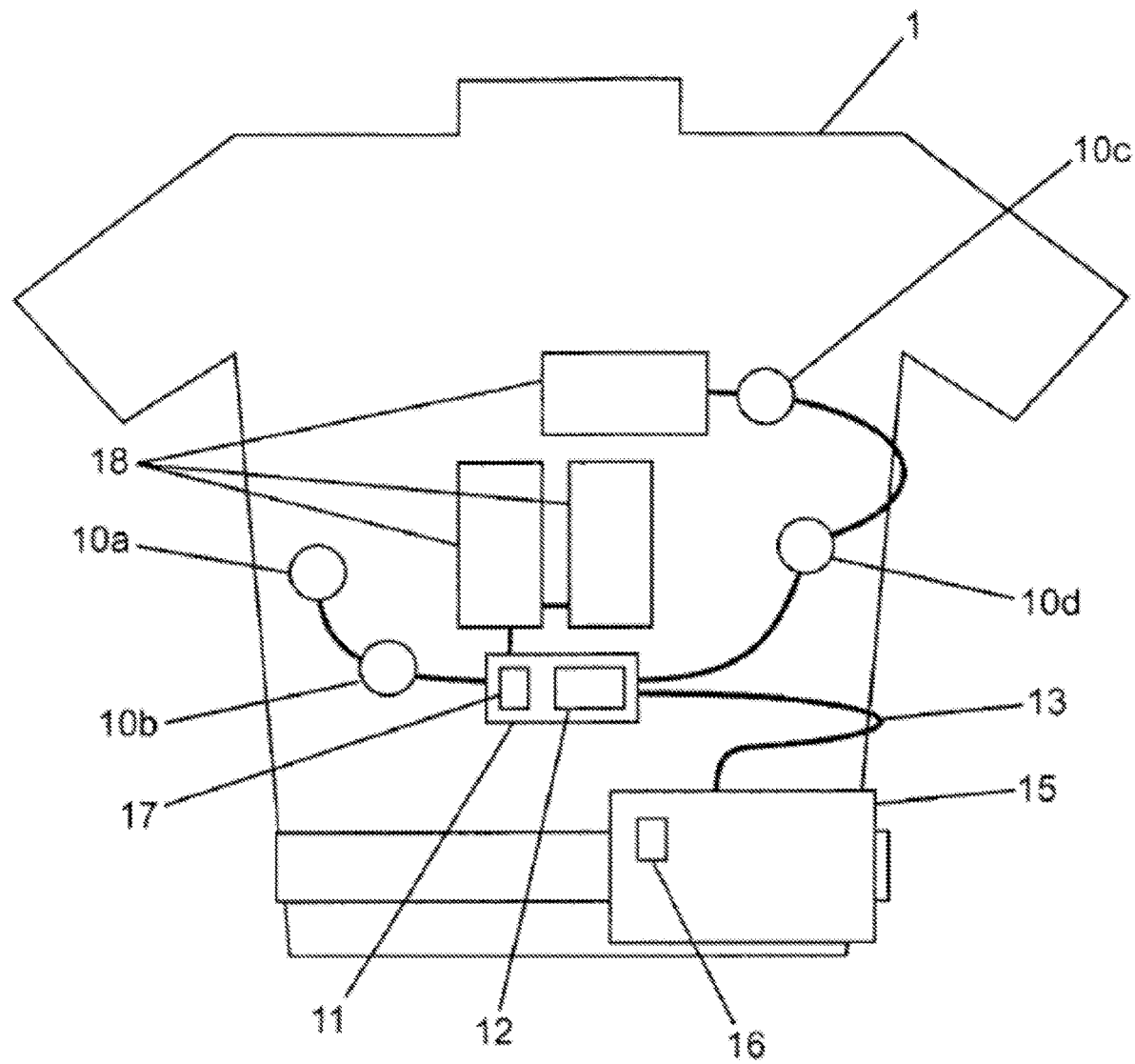
FIG. 3A is a schematic block diagram of one example of a wearable defibrillator.

FIG. 3A shows a patient 1 with a wearable defibrillator. Typically the wearable defibrillator shown would be worn as a vest, belt and/or other clothing. In this example, four sensing electrodes 10*a, b, c, d*, or physiological sensors are shown. These sensors are positioned adjacent to the body of patient and in proximity to the skin of the patient. While this example includes four cardiac sensing electrodes and is for cardiac monitoring and treatment, other medical functions could also be appropriately monitored or treated. In this example, a node, 11, is used and the sensors 10*a, b, c, d* and treatment devices 18 connect to the node. In this example, node 11 electrically couples the sensors 10*a*, 10*b*, 10*c* and 10*d*, and therapy pads or treatment devices 18 to a portable treatment controller in accord with the portable treatment controller 200 described above. The node 11 could be on the belt or on other patient locations. The therapy pads or treatment devices 18 provide treatment when a sensed condition indicates the desirability of a treatment. In some examples, the treatment devices 18 include an impedance reducing substance, such as an impedance reducing gel, that is automatically applied by the treatment device 18 prior to issuing a therapeutic shock to the patient.

This example of a wearable defibrillator also includes motion sensors. While various examples may use any motion sensor, in the present example, accelerometers are used. Such sensors indicate accelerating movements. Because of the nature of human movements, generally comprising short distance and short duration, accelerometers give a very acceptable indication of patient movement. Single axis accelerometers can be used as well as multi-axis sensors.

In this example, two accelerometers 16, 17 are used. One accelerometer 17 is located on the node 11 and a second 16 is used on the monitor 15 that includes the portable treatment controller 200. It is understood that some examples use a single accelerometer or position/force/motion detector, and still other examples may use three or more. Using multiple sensors permits the power conserving processor arrangement 100 to implement a treatment method that evaluates accelerometer (sensor) differentials and predicts patient activity and accelerometer reliability. The use of multiple accelerometers permits separate and independent evaluation of patient movements from multiple perspectives which, in turn, enables a multiple perspective comparison of the movements to best determine patient activity and equipment function. In addition, the use of multiple accelerometers, as opposed to a single accelerometer, allows the treatment method to better filter noise generated from patient motion or biological signals such as muscle noise. The actual treatment method used may depend upon the characteristics of the patient, the diagnostic requirement of each individual doctor, and the condition(s) he wishes to monitor. Any or all of the activities determined by the wearable defibrillator may be used for these functions. In addition, the accelerometers can be combined with other inputs, for example, to determine if one or more of the sensors 10*a*, 10*b*, 10*c* or 10*d* is no longer in intimate contact with the patient.

In this example, the node 11 also includes a tactile stimulator 12, which is a patient notification device. In some examples, the tactile stimulator 12 includes a motor with an unbalancing weight on this shaft. When the motor is on it causes the belt to vibrate much like a cell-phone in vibration mode.

Additionally, the treatment method executed by the power conserving processor arrangement 100 may accelerate or delay treatment. For instance, in some examples, the critical purpose processor 104 is configured to, upon detecting an abnormal condition, request that the general purpose processor 102 determine if the default treatment timeline should be adjusted. According to one example, the general purpose processor 102 is configured to make this determination by stimulating the patient, monitoring the patient for a response to the stimulus and adjusting the default treatment timeline based on the nature of the response received (or the lack thereof). In this example, the monitor 15 is configured to provide the stimulus via the user interface 208 or the therapy device interface 202. The stimulus may be any stimulus perceptible by the patient. Examples of stimuli that the monitor 15 may produce include visual (via a display included in the monitor 15), audio (via a speaker included in the monitor 15), tactile stimulation (via a vibrator device included in the node 11) or mild stimulating alarm shock (via the treatment devices 18).

Continuing this example, the general purpose processor 102 is configured to respond to the request for adjustment of the treatment timeline upon receipt and processing of a patient response. Patient responses may include any response that the monitor 15 is configured to process. Example responses include tactile responses (via a button, touch screen or other tactilely activated user interface element in the monitor 15), vocal responses (via a microphone in the monitor 15) and motion based responses (via the accelerometers 16 and 17).

In various examples, the general purpose processor 102 is configured to determine the type of adjustment to the treatment timeline and the magnitude of the adjustment based on the treatment urgency and patient readiness indicated in the patient response. For instance, in one example, the general purpose processor 102 is configured to respond with a decreased treatment timeline when the accelerometers 16 and 17 detect little or no motion from the patient in response to the stimulus. Alternatively, in this example, the general purpose processor 102 is also configured to delay treatment (increase the treatment timeline), or completely cancel treatment, when directed to do so by a user via the user interface 208. Thus, the general purpose processor 102 provides sophisticated user interface and patient monitoring functionality without impact to the critical purpose functions implemented using the critical purpose processor 104.

In other examples, the monitor 15 that includes the portable treatment controller 200 has a data storage 204 that is sized to store months or years of sensor information, such as ECG data, that is gathered over several monitoring and treatment periods. These monitoring and treatment periods may include continuous monitoring periods of approximately 23 hours (and substantially continuous monitoring periods of approximately 1-2 months) during which several treatments may be delivered to the patient. In some of these examples, the general purpose processor 102 is configured to analyze the stored sensor information and to determine adjustments to the treatment method, or alternative treatment methods, of benefit to the patient. For instance, in one example, the general purpose processor 102 is configured to analyze ECG data collected substantially contemporaneously with each instance of patient initiated delay, or cancelation, of treatment. In this example, the general purpose processor 102 is configured to analyze the stored months of ECG data to recognize individualized, idiosyncratic rhythms that, while not normal, do not indicate a need for treatment. In some examples, the portable treatment controller 200 may automatically adjust its treatment method to better suit the patient by not initiating treatment in response to the recognized, idiosyncratic rhythm. This adjustment may be performed in conjunction with review by appropriate medical personnel.

Thus, examples in accord with FIG. 3A provide for a wearable defibrillator that collects and stores substantial amounts of historical ECG information and that tailors its treatment method based on the stored information to provide superior patient care. In addition, the wearable defibrillator shown in FIG. 3A can be used in a variety of patient care scenarios where a conventional implantable cardioverter-defibrillator cannot. Examples of these scenarios include treatment when the patient is awaiting a pending transplant or where the patient has a systemic infection (e.g. influenza or osteomyelitis), myocarditis, intra-ventricular thrombus, cancer or a life-limiting serious illness such that an implantable device is not medically prudent.

In various examples disclosed herein, components read parameters that affect the functions performed by the components. For instance, in at least one example, the general purpose processor 102 is configured to read a parameter defining a particular reduced service state to assume after initialization. These parameters may be physically stored in any form of suitable memory including volatile memory (such as RAM) or nonvolatile memory (such as flash memory). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

In summary, examples disclosed herein provide for a processor architecture that provides a host of advantages when used in the context of a portable medical device. These advantages include enabling the portable medical device to provide advanced functionality while conserving electrical power, thereby increasing battery runtime and extending the useful life of the portable medical device. Other advantages include the ability to continuously monitor and store patient data over a prolonged duration without compromising the ability of the device to provide therapy when needed. In addition, the processor arrangement disclosed herein allows manufacturers of medical devices to isolate the components of the medical device that deliver critical functions involving patient care. This isolation promotes safe and reliable execution and allows new functions, which might otherwise destabilize the critical functionality, to be implemented using other components. Likewise, isolation of regulated functionality allows medical devices employing the processor arrangement disclosed herein introduce new features and functions without destabilizing components already approved by governmental agencies such as the FDA.

Energy Conserving Processes

Figure 4:
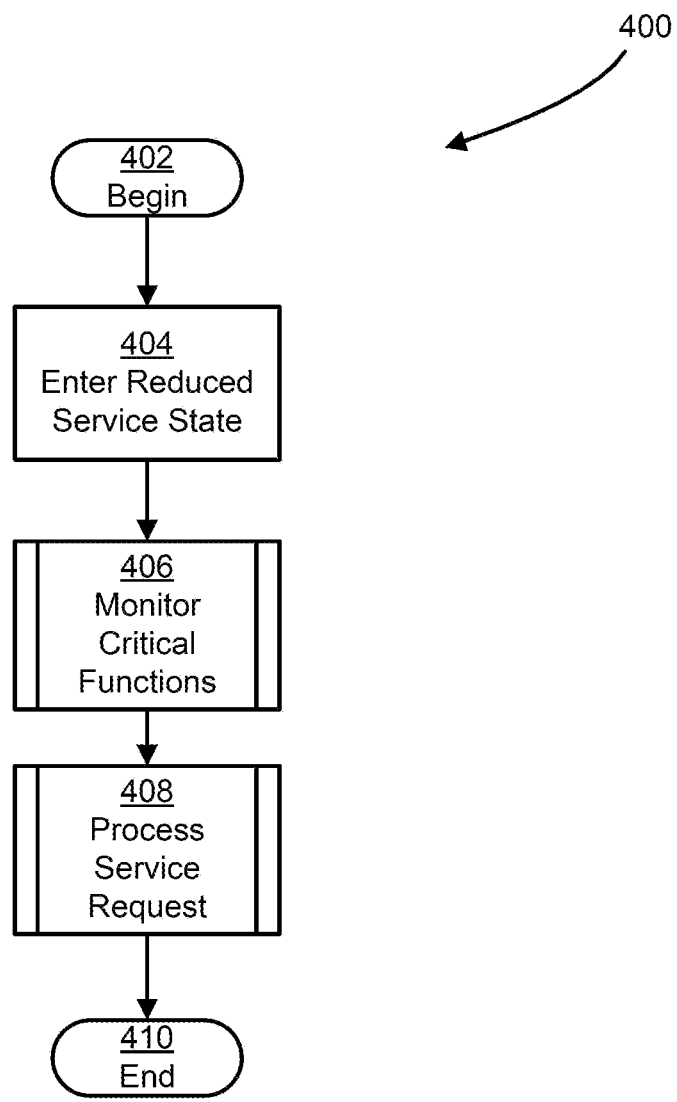
FIG. 4 is a flow diagram of one example of a method for conserving power used by a medical device using a processor arrangement.

Various examples provide processes through which a medical device conserves electrical energy while processing events and maintaining a history of data and events. In these examples, the medical device is arranged to include the power conserving processor arrangement 100 and specially configured to perform the functions disclosed herein. FIG. 4 illustrates one such process 400 that includes acts of entering a reduced service state, monitoring critical functions and processing events. Process 400 begins at 402.

In act 404, the medical device enters a reduced service state. According to some examples, the general purpose processor 102 enters the reduced service state upon determining that there are no unprocessed requests to act upon. This reduced service state is configurable and may include one or more processor performance or sleeping states.

In act 406, the medical device monitors critical functions. According to a variety of examples, the critical purpose processor 104 monitors the critical functions of the medical device. Acts in accord with these examples are discussed below with reference to FIG. 5.

In act 408, the medical device processes a service request. According to various examples, the critical purpose processor 104 causes the general purpose processor 102 to process the service request. Acts in accord with these examples are discussed below with reference to FIG. 6.

Process 400 ends at 410. Processes in accord with process 400 allow a medical device to perform its critical functions and to maintain a history of physiological data and events using components whose processing capabilities and power consumption are closely tailored to the tasks at hand. Thus, such processes allow the medical device to operate in an energy efficient manner.

Figure 5:
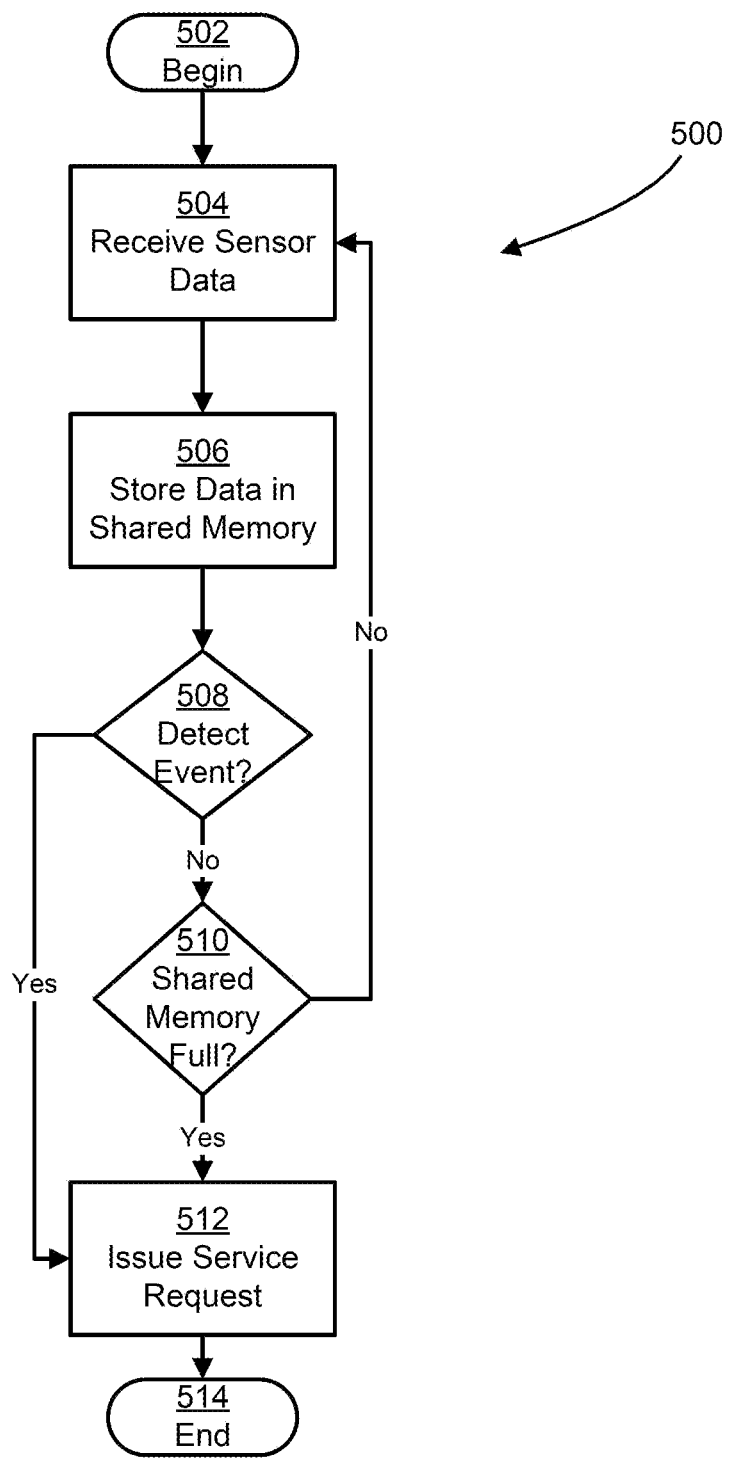
FIG. 5 is a flow diagram of one example of a method for monitoring critical functions of a medical device.

As discussed above with regard to act 406 shown in FIG. 4, various examples provide processes for monitoring the critical functions of a medical device. FIG. 5 illustrates one such process 500 that may be used to implement act 406 and that includes acts of receiving sensor information, storing the sensor information in shared memory, detecting an event and issuing a request for service. A medical device implementing process 500 begins at 502.

In act 504, the critical purpose processor 104 of the medical device receives sensor data via the sensor interface 212. In act 506, the critical purpose processor 104 stores the sensor data in the shared memory 106. In act 508, the critical purpose processor analyzes information including the sensor data and determines whether a critical event has occurred. If a critical event was detected by the critical purpose processor 104, the critical purpose processor 104 proceeds to act 512 when the method for processing the critical event includes functionality that the general purpose processor 102 is configured to provide, such as interacting with a user through the user interface 208. Otherwise the critical purpose processor 104 proceeds to act 510. In act 510, the critical purpose processor 104 determines if the shared memory 106 is full or if a predetermined amount of time (e.g. 5 minutes) has passed since the critical purpose processor 104 last issued a service request to the general purpose processor 102. If the critical purpose processor 104 determines that either of these conditions is true, the critical purpose processor 104 proceeds to act 512, otherwise the critical purpose processor returns to act 504. In act 512, the critical purpose processor issues a service request to the general purpose processor 102. A medical device implementing process 500 terminates the process at 514.

Processes in accord with process 500 enable medical devices that utilize the power saving processor architecture disclosed herein to isolate critical functions to particular components of the medical device. In this way, such processes increase stable and efficient execution of critical functionality.

Figure 6:
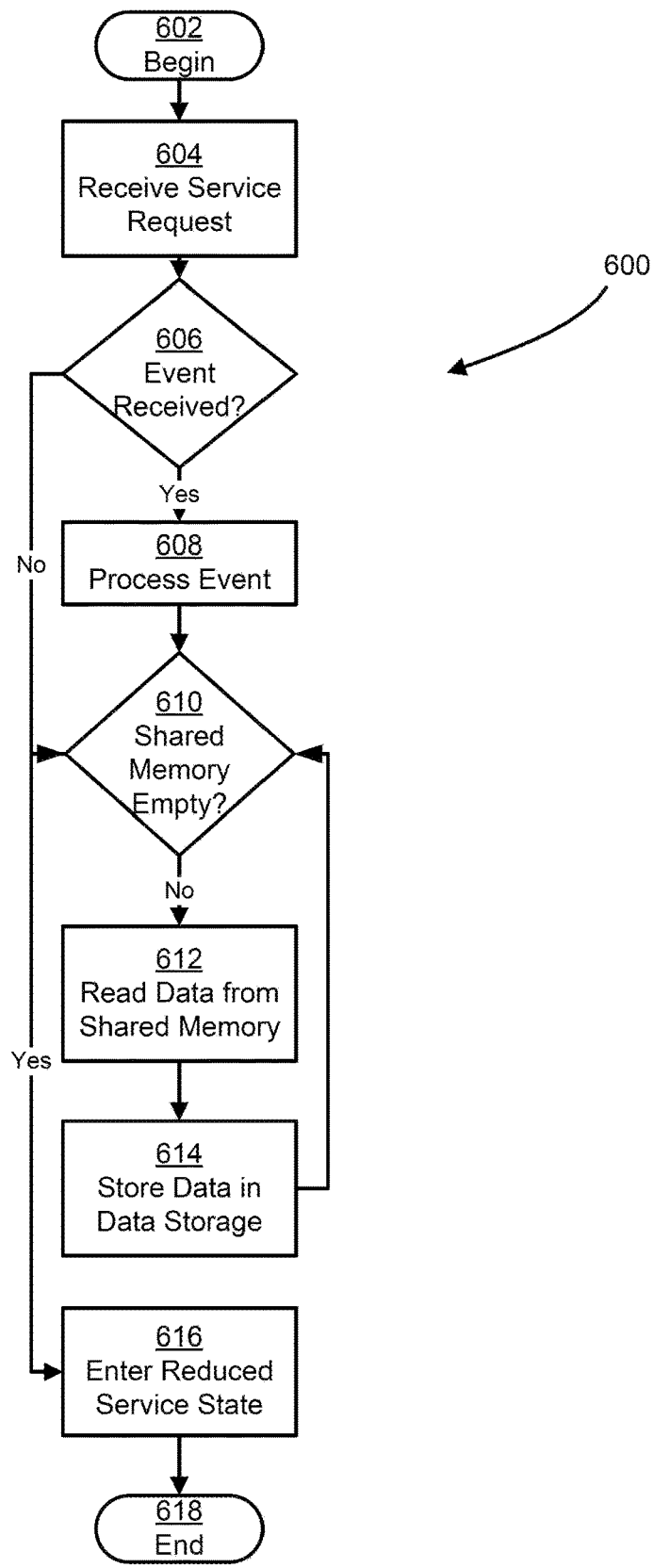
FIG. 6 is a flow diagram of one example of a method for processing a service request by made by a critical purpose processor.

As discussed above with regard to act 408 shown in FIG. 4, various examples provide processes for processing service requests in a medical device. FIG. 6 illustrates one such process 600 that may be used to implement act 408 and that includes acts of receiving a service request, reading data from shared memory, storing data in data storage, determining if the shared memory is empty, determining if a critical event was detected, processing critical events and entering a reduced service state. A medical device implementing process 600 begins at 602.

In act 604, the general purpose processor 102 receives a service request from the critical purpose processor 104. Upon receiving the service request, the general purpose processor 102 identifies a service state that provides the functionality required to process the service request and assumes the identified service state. In act 606, the general purpose processor 102 determines if a critical event was received from the critical purpose processor 104. If so, the general purpose processor 102 proceeds to act 608, which is discussed further below. Otherwise the general purpose processor 102 proceeds to act 610. In act 610, the general purpose processor 102 determines if the shared memory 106 is empty. If so, the general purpose processor 102 proceeds to act 616, otherwise the general purpose processor 102 proceeds to act 612. In act 612, the general purpose processor 102 reads data from the shared memory 106. In act 614, the general purpose processor 102 stores the data read in act 612 in the data storage 204 and returns to act 610. In act 616, after processing of the service request, the general purpose processor 102 enters a reduced service state to conserve power. A medical device implementing process 600 terminates the process at 618.

In act 608, the general purpose processor 102 performs a process that is responsive to the critical event received from the critical purpose processor 104. The particular acts included in the response process vary, depending upon the particular critical event received. For instance, in some examples, if the critical event is a cardiac dysrhythmia, the general purpose processor 102 conducts a responsiveness test to determine if the user should not have a therapeutic shock administered by the medical device and returns the results of the responsiveness test to the critical purpose processor 104. While conducting this responsiveness test, the general purpose processor 102 provides the user with 25 seconds to respond. In other examples, the general purpose processor 102 warns bystanders to step back and not interfere with the functioning of the device.

Processes in accord with process 600 enable medical devices that utilize the power conserving processor architecture disclosed herein while selectively leveraging the processing power of the general purpose processor 102. Thus, processes in accord with process 600 provide medical devices with a robust computing platform in a power efficient manner. In these and other examples, the general purpose processor 102 performs many functions other than process 600 and examples are not limited to a particular set of processes or functions.

In addition, each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein.

Additional Processor Arrangements

In some examples, a medical device comprises a processor arrangement that distributes processing between a dual core processor and a single core high voltage processor (HVP). The dual core processor includes a first core (application core) with an architecture and instruction set designed for application level processing and a second core (signal processing core) with an architecture and instruction set designed for signal processing. In certain implementations, the first core is an Advanced RISC Machine (ARM) core, and the second core is a digital signal processor (DSP) core. In general, the signal processing core receives physiologic data from one or more physiologic sensors of the medical device (e.g., ECG electrodes), relays the physiologic data to the application core, and transmits an output (e.g. a synchronization control signal) to the HVP for synchronizing defibrillation. The application core receives data descriptive of electric signals indicative of a patient's cardiac activity (e.g. ECG data), performs ECG analysis using the ECG data, executes user interface (UI) communication, and performs other high-level processing functions in the medical device.

Figure 7:
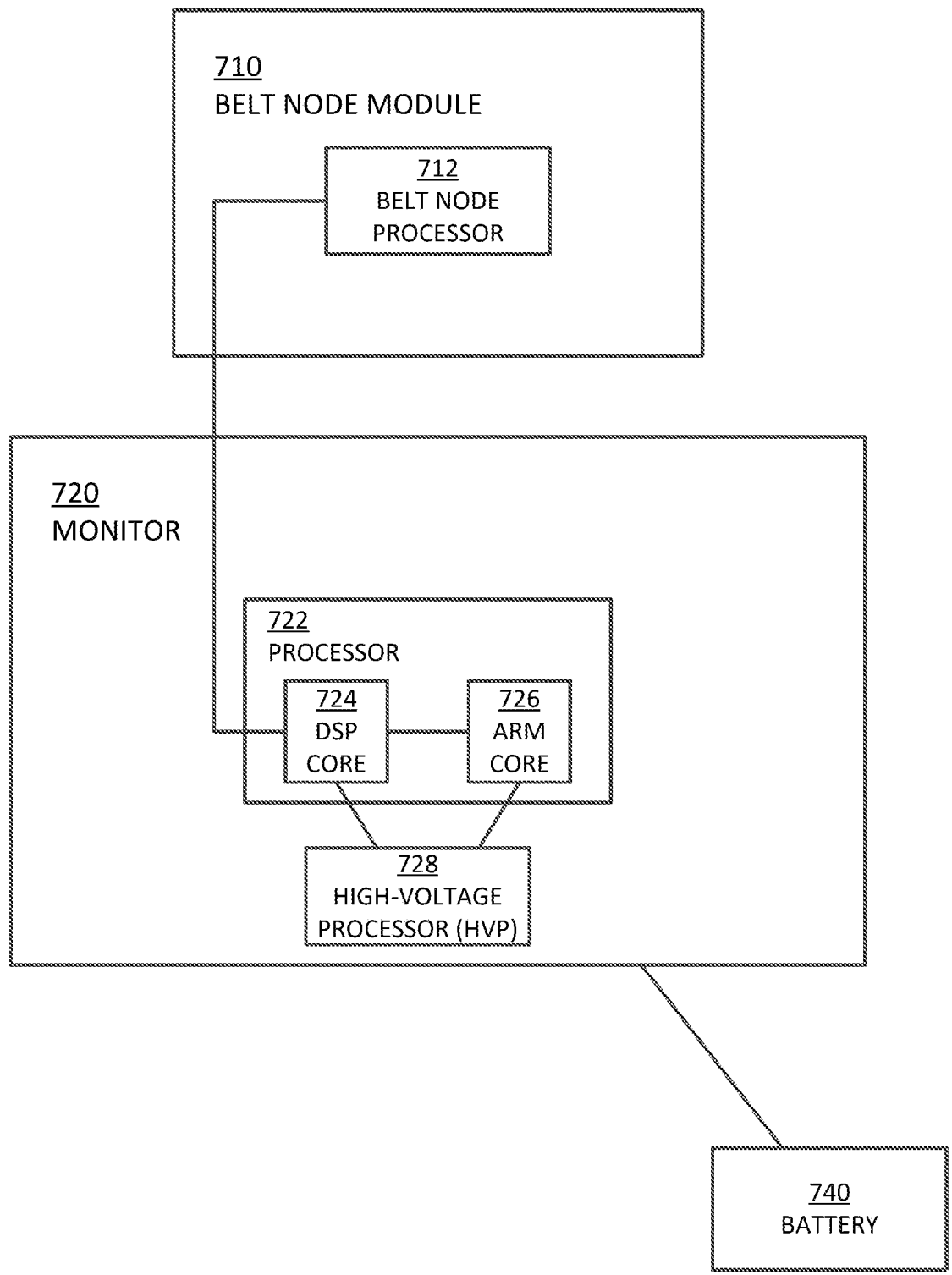
FIG. 7 is a schematic block diagram of one example of a portable medical device having a dual-core processor and a high-voltage processor.

In at least one example, the distributed processor arrangement, and more particularly the signal processing core, communicates with a belt node processor of a belt node module (e.g., the belt node 11 described above with reference to FIG. 3A or belt node module 710 described herein with reference to FIG. 7). In this example, the medical device monitors and/or treats Ventricular Tachycardia (VT), Ventricular Fibrillation (VF), and/or other cardiac arrhythmias. More specifically, when in use in this example, the medical device continuously records ECG data, monitors the ECG data to determine whether defibrillation is warranted, and executes defibrillation if warranted.

Reference is now made to FIG. 7 showing a schematic block diagram of one example of a portable medical device having a dual-core processor and an HVP. As shown, the portable medical device includes a belt node module 710 (e.g. node module 11 shown in FIG. 3A), a monitor 720 (e.g. monitor 15 shown in FIG. 3A), and a battery 740. The belt node module 710 includes a belt node processor 712. The monitor 720 includes a dual core processor 722, and an HVP 728. The dual core processor 722 includes a DSP core 724 and an ARM core 726. As shown in FIG. 7, the belt node processor 712 is coupled to the DSP core 724 via a bidirectional communication path. The DSP core 724 is coupled to the ARM core 726 via a bidirectional communication path. The HVP 728 is coupled to the DSP core 724 and the ARM core 726 via a bidirectional communication path. Specific examples of these communication paths are described further below.

In various examples, the belt node module 710 is configured to acquire physiologic signals (e.g. ECG signals) from a patient and transmit data descriptive of the physiologic signals to the monitor 720 via a communication path. In these examples, the monitor 720 is a portable device that is connected to the belt node module 710 and powered by the battery 740. The monitor 720 is configured to receive the physiologic data, process the data to determine whether treatment of the patient is warranted, and where treatment is warranted, treat the patient (e.g., by delivering a therapeutic shock to the patient).

Figure 8:
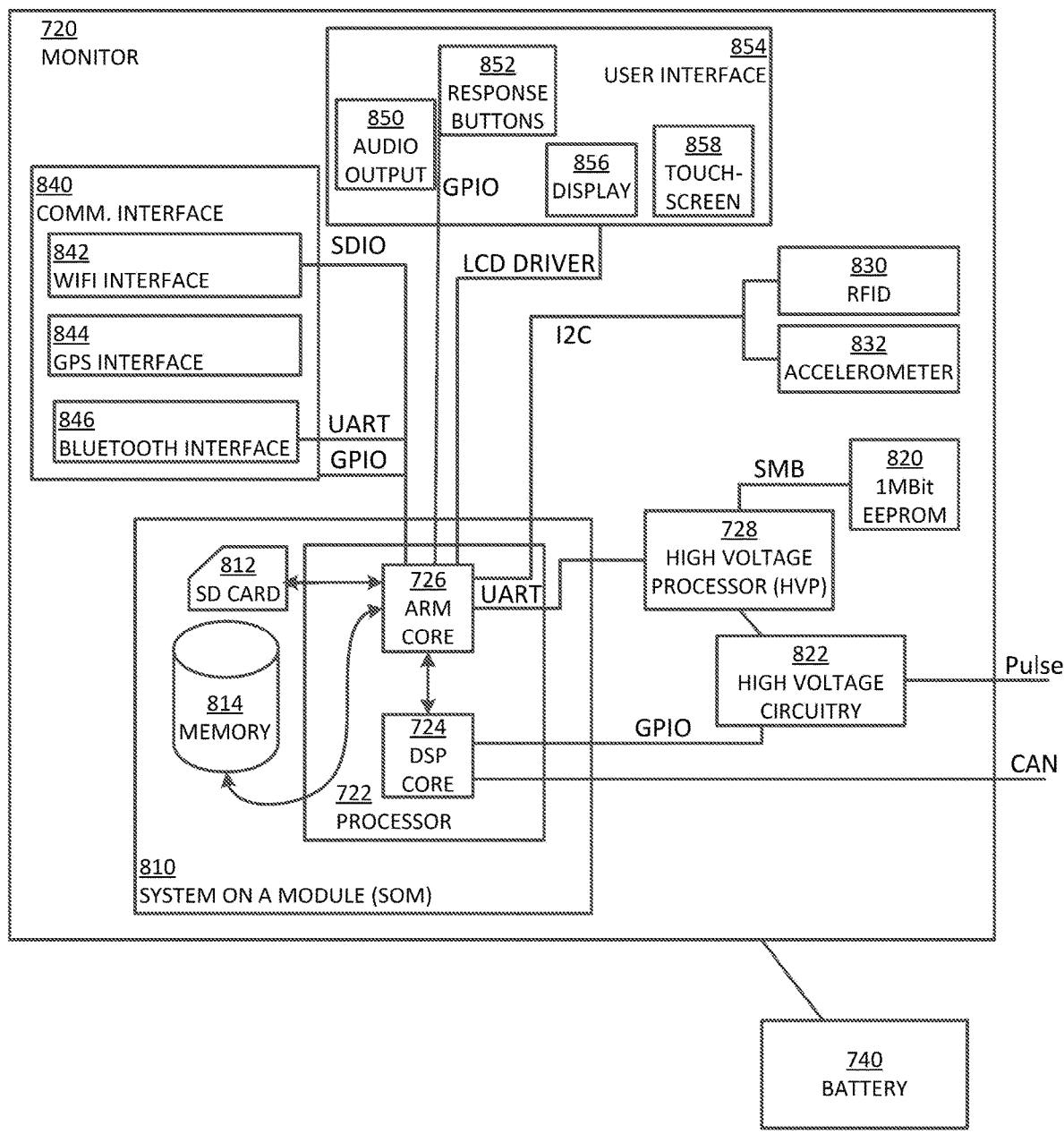
FIG. 8 is a schematic block diagram detailing one example of a portable medical device.
Figure 9:
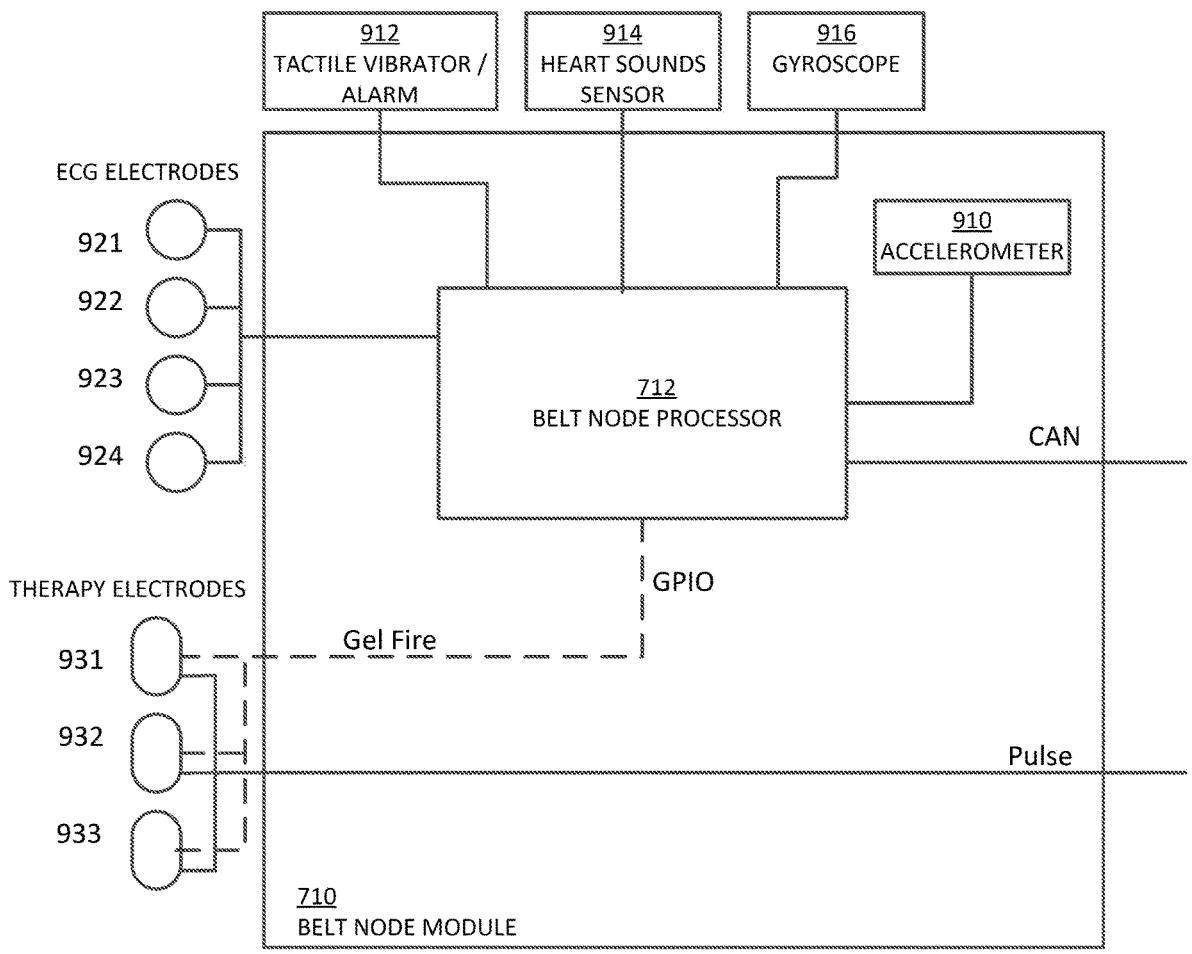
FIG. 9 is a schematic block diagram detailing one example of a belt node module.

For instance, in one example in accord with FIG. 7, the belt node processor 712 is in communication with the dual core processor 722, and more particularly with the DSP core 724. In this and other examples, the belt node processor 712 runs a scheduling loop that iteratively acquires and transmits ECG signals. The belt node processor 712 acquires the ECG signals, digitizes the ECG signals into ECG data, and streams the ECG data to the monitor over a communication path (e.g. a CAN bus coming from DSP core 724 as shown in FIG. 8 communicating with CAN bus from the belt node processor 712 as shown in FIG. 9). In some examples, the belt node processor 712 also controls a tactile alarm (shown and described below with reference to FIG. 9) and controls the deployment of electrically conductive gel (to the therapy delivery devices) as part of a treatment protocol.

Continuing with the example of FIG. 7, the DSP core 724 of the monitor 720 receives and processes CAN communication packets from the belt node processor 712. In some examples, this processing includes receiving ECG data (and heart sounds data in an example) and transmitting the ECG data to the ARM core 726. In some examples, the ARM core 726 implements an operating system and is configured to control of start-up and shutdown of the medical device, host several specialized application processes, and provide inter-process and network communication services. For instance, in one example, the ARM core 726 includes a Signal Processing Algorithm (SPA) subsystem. The SPA subsystem is responsible for performing one or more functions, such as ECG analysis, arrhythmia detection, determination of whether a defibrillation pulse is necessary, and, if necessary, overall control of therapy.

Continuing with the example of FIG. 7, the ARM core 726 analyzes the ECG data and determines whether defibrillation is warranted. If defibrillation is warranted, the ARM core 726 transmits a treatment control signal to the HVP 728 and the DSP core 724. In response to receipt of this treatment control signal, the HVP 728 and the DSP core 724 prepare the medical device for delivery of therapy as is described further below.

In some examples, the DSP core 724, in response to receiving a treatment control signal from ARM core 716, analyzes the incoming ECG data and synchronizes a defibrillation pulse to the patient's R wave. In these examples, to initiate the defibrillation pulse at the appropriate, synchronized time, the DSP core 724 transmits a synchronization control signal over a CAN bus to the HVP 728. By synchronizing the defibrillation pulse to the patient's R wave, the medical device may avoid triggering another arrhythmia or other undesirable cardiac condition.

The HVP 728 is configured to manage the high voltage circuitry for patient defibrillation. In an example, the HVP 728 contains and isolates safety critical software (Class C) from other components of the medical device. In certain implementations, the HVP 728 can implement a scheduling loop (e.g., a control loop with interrupt service routines), and thus can operate without a Real Time Operating System. This architecture can reduce system complexity and improve software reliability. In some examples, the HVP 728 is configured to control of the high voltage circuitry (e.g., charging and discharging of one or more capacitors), control timing of defibrillation pulse delivery for synchronization, and control and/or modify an amount of pulse energy to deliver. In at least one example, the HVP 728 subsystem can be configured as a slave to the ARM core 726. In this example, the HVP 728 can communicate with the ARM core 726 via serial communication.

In accordance with an example, there are a number of different levels of processing models implemented levels within the portable medical device. These can include a real time processing model, an event based processing model, an intermittent processing model, and an application level processing model. To be safe and effective, functionality related to patient treatment must be executed according to strict timing requirements. For example, defibrillation pulses can be processed in real time to be safe and effective in operation. Event based processing occurs at higher levels of the system, including the SPA. These events generally should be addressed in near real time. Intermittent processing includes the daily downloads of the system log data. Application level processing is a type of intermitted processing and an example is the daily processing of heart sound or other physiological data (e.g. ECG data) for systems equipped to monitor physiological data. The physiological data is acquired by the ARM core 726 and processed by the ARM core 726 to determine if treatment is necessary.

Two of the physical components of the therapeutic medical device include the monitor, shown in detail in FIG. 8, and the belt node module, shown in detail in FIG. 9. The monitor includes a dual core processor and a single core processor.

The belt node module includes a belt node processor that digitizes the ECG data and passes it to the monitor via a Controller Area Network (CAN) bus.

Monitor

Reference is now made to FIG. 8 showing a schematic block diagram detailing one example of the monitor 720. The monitor 720 can include a dual core processor 722 implemented as a system on a module (SOM) 810, an RFID module 830, an accelerometer 832, a communication interface 840, and a user interface 854 in an example. The SOM 810 can also include an SD card 812 and memory 814. The memory 814 can be a non-transitory and non-interchangeable computer readable medium, and can contain all system files necessary for operation of the ARM core 726 and, in some examples, patient data. The non-interchangeable memory 814 can reside on the main PCB (e.g. SOM 810 in FIG. 8). In an example, the memory 814 is organized into a transactional file system (e.g., Unsorted Block Image File System) that ensures integrity of the file system in the event of a power loss. The SD card 812 exchanges data with the ARM core 726 and is used to record patient monitoring data (e.g. ECG data and treatment data). This data is used for further processing by the ARM core 726, or transmitted to other devices, for example over the communication interface 840, for additional processing and management of the patient monitoring data.

The monitor 720 includes a 1 Megabit EEPROM 820 that communicates with the HVP 728 using a Server Message Block (SMB) protocol. The HVP 728 communicates with high voltage circuitry 822 to determine the appropriate pulse to deliver via the therapy delivery device. The high voltage circuitry 822 is in communication with the DSP core 724 of the dual core processor 722 over a General Purpose Input/output (GPIO) interface. The monitor 720 delivers biphasic defibrillation pulses from the high voltage circuitry 822. The biphasic defibrillation pulses include energy in the range of 75 joules to 150 joules in 25 joule increments.

The monitor 720 includes an RFID module 830 and an accelerometer 832 that communicate with the ARM core 726 using the Inter-Integrated Circuit (I2C) protocol. The DSP core 724 also communicates over the CAN bus to the belt node processor 712 (shown in FIG. 9). The RFID module 830 is configured for near field communication of an identifier of the medical device to RFID-enabled devices. The accelerometer 832 is used to acquire analog signals descriptive of heart sounds, can be a MEMS accelerometer in one example, and can be used to track patient movement in one example.

As shown in FIG. 8, the monitor 720 includes a communications interface 840. The communications interface 840 includes various interfaces for external communication. As shown, these interfaces include a Wi-Fi® interface 842 for communicating to a Wi-Fi® network proximate the medical device, a GPS interface 844 for communicating with global positioning system facilities, and a BlueTooth® interface 846 for communicating with Bluetooth® enabled devices. The Bluetooth® interface 846 can be any appropriate short range communication interface in accordance with the techniques herein for short range wireless communication with other devices. The ARM core processor 726 controls the Wi-Fi® interface 842 using a Secure Digital Input Output (SDIO) protocol. The interface between the Bluetooth and the ARM core 726 occurs over Universal Asynchronous Receiver/Transmitter (UART). There is also provided a General Purpose Input Output (GPIO) interface between the ARM core 726 and the communications interface 840 to allow for a general input or output between the communications interface 840 and the ARM core processor 726.

A user interface 854 is included in the monitor 720, which has an audio output 850, response buttons 852, a display 856, and a touchscreen 858. The user interface 854 is under control of the ARM core 726 of the dual core processor 722. The user interface 854 is configured to, in operation, receive all of the user inputs to the touch screen 858 and transmit screen displays to the display 856, run the user interface state machine, and control the audio output 850. The audio output 850 is configured to provide an audio signal to the patient and deliver an alarm or other appropriate messages. The one or more response buttons 852 are in communication with the ARM core 726 over a GPIO interface. As described herein, the response buttons 852 can be used to control timing of the treatment or therapy that is delivered to the patient. In one example operation, the portable medical device can include two response buttons and both are required to be pressed to defer treatment where an arrhythmia has been detected. Where a user interface (or the user) becomes impaired, a single response button mode can be enabled which is configured to defer treatment via a single button press.

The operating system of the monitor is custom and includes drivers for the medical device. A touch screen driver provides an interface, which can be a serial interface, that is used to capture user input. A display driver or graphics library can be used to implement the user interface. An I2C driver is used for communication with the hardware device, for example the RFID module 830 and accelerometer 832.

The monitor 720 includes various interconnection mechanisms. For example, a CAN bus is provided between the DSP core 724 and the belt node processor 712. The CAN bus transports data between the DSP core 724 and the belt node processor 712. This data may include software updates sent from the DSP core 724 to the belt node processor 712 and ECG data sent from the belt node processor 712 to the DSP core 724. In another example interconnection mechanism, signals between the ARM core 726 and the HVP 728 are carried over a serial data link (on printed circuit board (PCB), without requiring external cabling). The messages over this interconnection mechanism include high voltage charge or drain commands from the ARM core 726 to the HVP 728, and therapy electrode "fall-off" indications from the HVP 728 to the ARM core 726.

In some examples, a fall-of signal, which may be transmitted at 800 Hz signal, can be used to detect whether the electrodes are properly positioned to acquire ECG signals. By monitoring for this signal, the ECG electrode can indicate to the DSP core when the ECG electrode is not in the proper position. Similarly, a therapy electrode can indicate when the therapy electrode is not in the proper position by detecting the 800 Hz signal is absent and transmitting a fall-off indicator when the 800 Hz signal is not detected. Accordingly, there is a therapy electrode fall-off indicator that indicates that one or more of the therapy electrodes are not in proper contact with the patient, and also a physiologic sensor fall-off indicator that indicates that one or more of the ECG electrodes are not in proper contact with the patient. The therapy electrode fall-off indicator can be used to determine whether the therapy electrode is in the proper position to apply a treatment sequence. If the therapy electrode fall-off indicator is present, then the HVP 728 will not initiate a treatment sequence, because the therapy electrode is not properly positioned. If the physiological sensor (e.g. ECG electrode) indicates the electrode is not in the proper position, this can indicate that the detection of ECG signals is not accurate, and a treatment sequence should not be initiated until the proper ECG signals are acquired. When the electrodes are in the proper position, the fall-off signal will be captured. Detection of the fall-off signal is performed by hardware within the belt node processor using a high-pass filter and an accumulator. To determine the status of the electrodes, the output of the accumulator is digitized and compared to a threshold.

In some examples, the ARM core 726 notifies the DSP core 724 of a need to defibrillate and the DSP core 724 uses a direct GPIO output to send the synchronization control signal to trigger the HVP 728 to defibrillate at an appropriate time. The data between the DSP core 724 and the ARM core 726 is carried over an internal (i.e. on-chip) data link that is data message based. The messages over the DSP/ARM communication link include sending ECG data packets from the DSP core 724 to the ARM core 726, and sending a message to initiate a treatment sequence from the ARM core 726 to the DSP core 724.

Belt Node Module

Reference is now made to FIG. 9 showing a schematic block diagram detailing one example of a belt node module 710. The belt node module 710 includes a belt node processor 712. Like the HVP 728, the belt node processor 712 runs a scheduling loop with specific interrupt routines. The primary function of the belt node processor is to digitize the ECG signals acquired by the ECG electrodes 921, 922, 923, 924 and pass the digitized data to the monitor 720 via the CAN bus. The belt node processor 712 is configured to trigger the release of electrically conductive gel from the therapy electrodes 931, 932, 933. In the example shown, the belt node processor 712 triggers deployment of the gel via a GPIO interface. The therapy electrodes 931, 932, 933 are configured to deliver treatment (e.g., defibrillation) by conveying electric pulses received from the high voltage circuitry 822. In one example, the belt node processor 712 can be an ARM based microcontroller (MCU) and in another example, the belt node processor 712 can be a mixed-signal MCU coupled to a DSP processor.

In some examples, the belt node module 710 includes an accelerometer 910 to determine movement of the belt node module and provide the information to the belt node processor 712. The movement of the accelerometer can be used to discount false indications of a medical condition and also to track patient movement. The belt node processor 712 collects heart sounds data from the heart sounds sensor 914, and gyroscope data from the gyroscope 916 and provides this data to the DSP core 724 for analysis and processing.

The belt node module 710 uses visible, audible and tactile alarms when it has determined that treatment (e.g. defibrillation) is necessary. These alarms provide the user with the ability to override the delivery of therapy in the event that, for example, cardiac performance is not sufficiently compromised. This can include a tactile vibrator or alarm 912. In an example, the DSP core 724 communicates with the belt node processor 712 over a CAN bus (as shown in FIGS. 8 and 9) using a command/response and data transfer protocol.

Software Architecture

Figure 10:
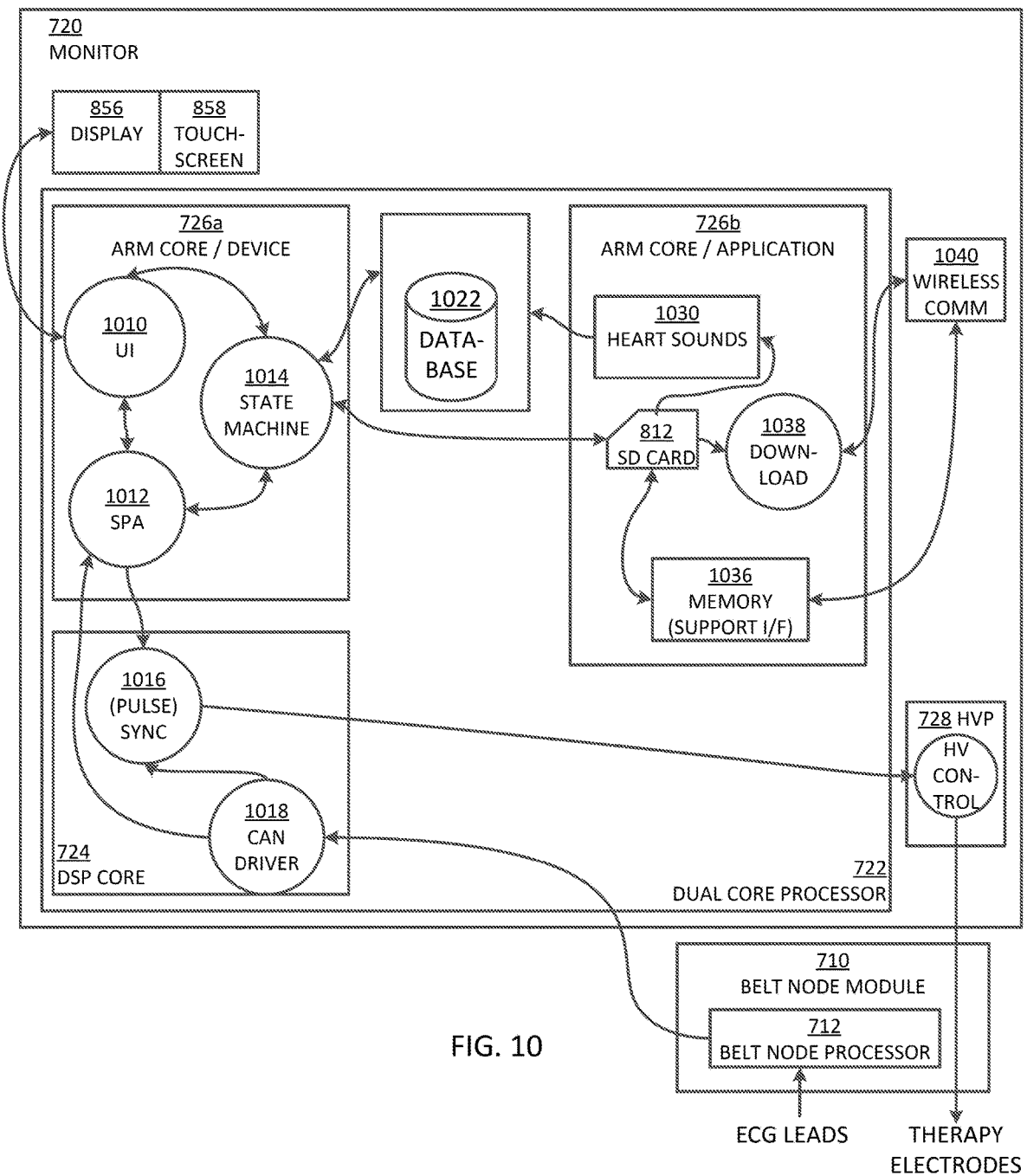
FIG. 10 is a functional block diagram showing the hardware architecture and associated software decomposition.

Reference is now made to FIG. 10 which is a functional block diagram showing the hardware architecture and associated software decomposition for the monitor having a distributed architecture arrangement. In the diagram, the monitor 720 is shown with the various device and application components segregated for illustrative purposes only. Note that the ARM core 726 of the dual core processor 722 is represented as the ARM core device 726*a* and the ARM core application 726*b* to show the different software processes executed by the ARM core 726. The ARM core 726*a* includes a User Interface process 1010 in communication with a display 856 and touchscreen 858. The ARM core 726*a* includes the SPA interface 1012 and the state machine component 1014. The state machine component 1014 is configured to control the overall system and control therapy delivery via a treatment sequence. The dual core processor 722 also includes a database 1022 of system files and patient data (e.g., as stored in the memory 814).

The ARM core application 726*b* includes heart sounds component 1030 that processes heart sounds data stored on the SD card 812 and stores heart sounds and/or other patient information in the database 1022. Data on the SD card 812 can also be sent by a download application 1038, via wireless communication 1040, to an external source. The ARM core 726*b* also includes memory 1036 that communicates with the SD card 812 and the wireless communication 1040.

The DSP core 724 includes a synchronization control interface 1016 that communicates with the SPA 1012 of the ARM core 726*a* and receives data from the CAN driver 1018. The synchronization control interface 1016 transmits a synchronization control signal to the HV control of the HVP 728. In response to receiving the synchronization control signal, the HVP 728 delivers an electrical (e.g., defibrillating) pulse to the therapy electrodes. Signals from the ECG leads are delivered to the belt node processor 712. The belt node processor 712 provides ECG data based on the signals from the ECG electrodes to the CAN driver 1018. The CAN driver 1018 indicates to the SPA 1012 and the sync interface 1016 the condition of the patient based on the signals received from the ECG electrodes so that the appropriate therapy can be administered by the therapy electrodes.

Software Architecture—SPA/DSP Subsystem

Figure 11:
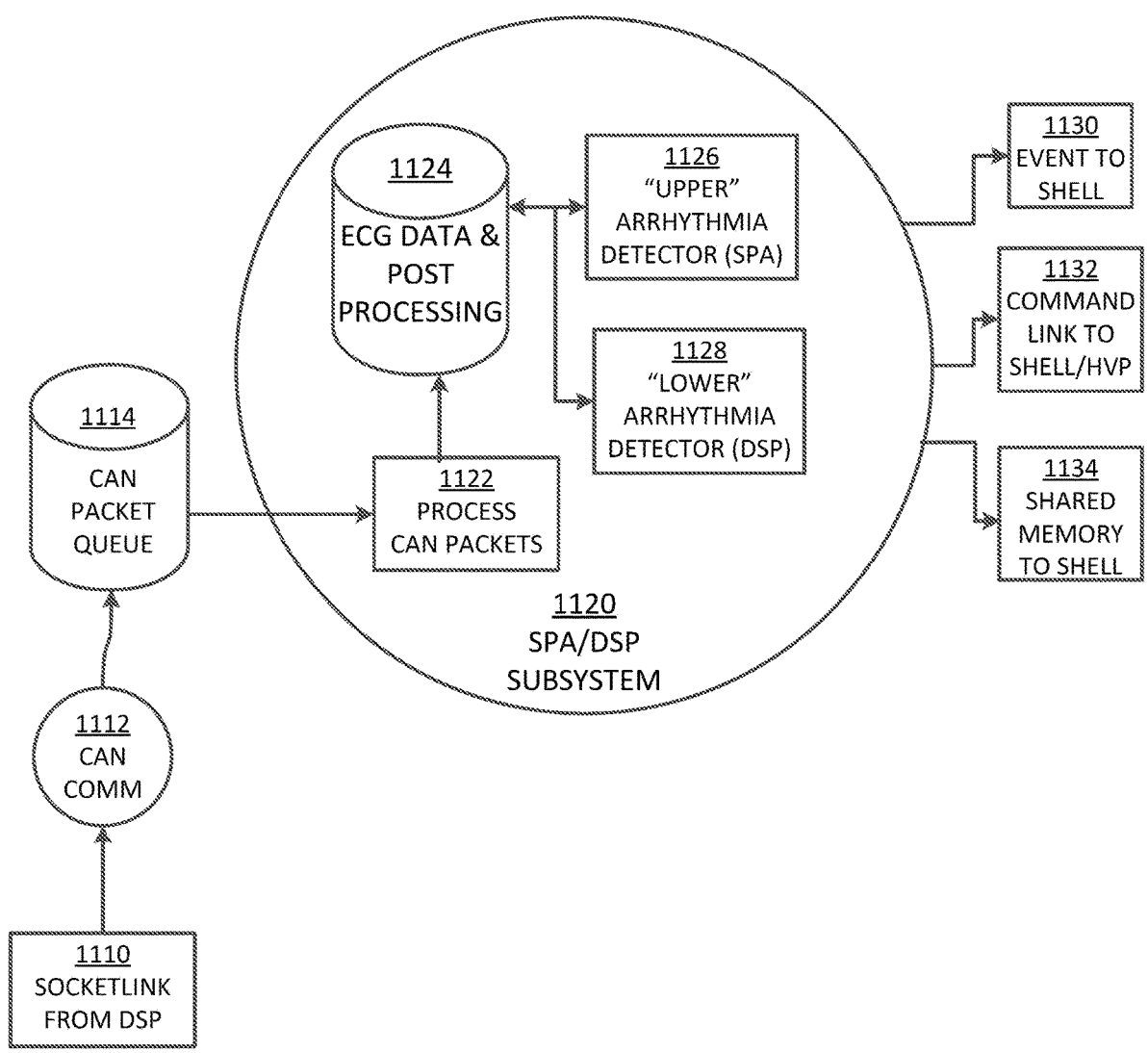
FIG. 11 is a functional block diagram of the signal processing algorithm (SPA) and digital signal processing (DSP) subsystem.

Reference is now made to FIG. 11 showing a functional block diagram of the signal processing algorithm (SPA) and digital signal processing (DSP) subsystem. The SPA is configured to receive incoming CAN packets containing ECG data, analyze the ECG data, determine when fibrillation is necessary, and execute any needed treatment sequence. The SPA/DSP software subsystem 1120 can run on the ARM core of the dual core processor in accordance with the techniques disclosed herein. The SPA/DSP subsystem 1120 includes the following types of elements: communication buffers, threads for processing, and data stores. The data stores include a CAN packet queue 1114 and ECG data and post processing 1124.

In certain implementations, there can be at least four communication buffers within the SPA/DSP system 1120, including a SocketLink to DSP core buffer 1110, a CommandLink to Shell Process/HVP Processor buffer 1132, a SharedMemory to Shell buffer 1134, and an Event to Shell buffer 1130. The SocketLink interface buffer 1110 stores the Shell/DSP subsystem communications with the DSP Core 724. The SocketLink communication buffer stores CAN packets holding inbound ECG data, Heartsound data and accelerometer data. In some examples, the SocketLink communication buffer 1132 receives the CAN packets from the DSP core 724. The SocketLink communication buffer also stores outbound CAN packets including requests to check gel status and/or control gel firing.

The CommandLink communication buffer provides a mechanism for the shell to control the runtime configuration of the SPA/DSP software subsystem. The CommandLink communication buffer is used to communicate and configure important parameters, such as patient's morphology baseline used by the detection algorithm as well as the state of various features implemented in the SPA/DSP component, such as single response button mode.

The SharedMemory communication buffer contains status information from the detection algorithm interleaved with the ECG stream. The output from this stream is typically written into a holter file. The output data is useful for the ARM core 726 when analyzing the performance of the SPA/DSP software.

The Event communication buffer is used to communicate actionable determinations made by the SPA/DSP components. For example, detected arrhythmias are indicated by data stored in this communication buffer as well as noise that might interfere with the algorithm. The Event communication buffer also transports updates when the belt connection status changes and when the flag queue needs to be serviced.

The CAN communication module runs its own thread in accordance with an example. The CAN communication module 1112 is responsible for reading incoming packets from the DSP processor via SocketLink communication buffer 1110. The CAN communication module 1112 receives the packets and puts them in a CAN packet queue 1114 for the SPA/DSP thread to read from. By providing the queue, this ensures that the data packets are read from the CAN interface before a data overrun can occur.

The SPA/DSP arrhythmia detection subsystem 1120 runs its own thread in accordance with an example. The Process CAN packets module 1122 is configured to de-queue any CAN packets in the CAN packet queue 1114. CAN packets containing ECG data are parsed and the ECG data is inserted in the ECG data and post processing data store 1124. The arrhythmia detection runs in a detection thread. The actual arrhythmia detection code is split into two parts that are referred to as the "upper" arrhythmia detector (SPA) 1126 and the "lower" arrhythmia detector (DSP) 1128. The lower arrhythmia detector 1128 has the function of performing a base ECG rate detection and determination of Ventricular Fibrillation (VF), Ventricular Tachycardia (VT), Asystole or more normal rhythms. The lower arrhythmia detector 1128 can be referred to as the "DSP" level due to its focus on the digital signal processing. The upper arrhythmia detector 1126 has the function of determining the appropriateness of doing treatment and drives the treatment sequence based on the ECG data. This is referred to as the "SPA" level due to the signal processing algorithm that the upper arrhythmia detector 1126 performs.

Based on the results of the upper arrhythmia detector 1126, messages will be sent to the Shell and the HVP via the event communication buffer 1130. These events can affect the current state of the therapeutic medical device. For instance, they can cause the therapeutic medical device to start a treatment sequence or to notify the patient of the presence of noise. The CommandLink communication buffer transports messages to control runtime configuration of the Shell/HVP 1132. ECG signals and system status message are sent to the Shell via the SharedMemory interface 1134 and are recorded in the holter file. These can be used by the ARM core 726 for analysis of the detection engine's performance.

The upper and lower arrhythmia detection is performed by the SPA/SPA subsystem 1120 that is implemented by the ARM core 726 of the dual core processor 722. Thus, the SPA/DSP subsystem processing is performed by the ARM core 726, and the decision logic is performed by the DSP core 724 of the dual core processor 722 to provide the synchronization signal to the HVP at the appropriate time. The arrhythmia detection system operates in a multi-layer architecture, where the first layer involves applying digital signal processing techniques to harvest information about the heart. The harvested information can then be analyzed in a second layer, and the data from the first layer and the second layer is fed into a decision logic which will determine if the arrhythmia is present. In an example, the decision logic can examine noise status from a noise analyzer and proceed accordingly. If a noise free condition is present, the decision logic executes a dual arrhythmia test. If noise is detected on one of the channels, then a single arrhythmia test is executed.

The DSP portion (lower arrhythmia detector) 1128 utilizes two ECG channels in an example. The ECGs are captured differentially via four ECG electrodes in an example, each having a bandwidth of approximately 1-MHz-2.4 kHz. Before the ECG data is digitized, the ECG is passed into a band pass filter (which can be 0.5 Hz-40 Hz) and dynamic amplifier. The amount of amplification is software controlled to ensure that the arrhythmia detection and noise detection modules work with optical ECG levels. In certain implementations, the processed ECGs can be offset approximately 2.048 V to accommodate the use of 16-bit unipolar A/D (analog-to-digital converter) with a dynamic range of 0-4.096 V.

Software Architecture—DSP Core

Figure 12:
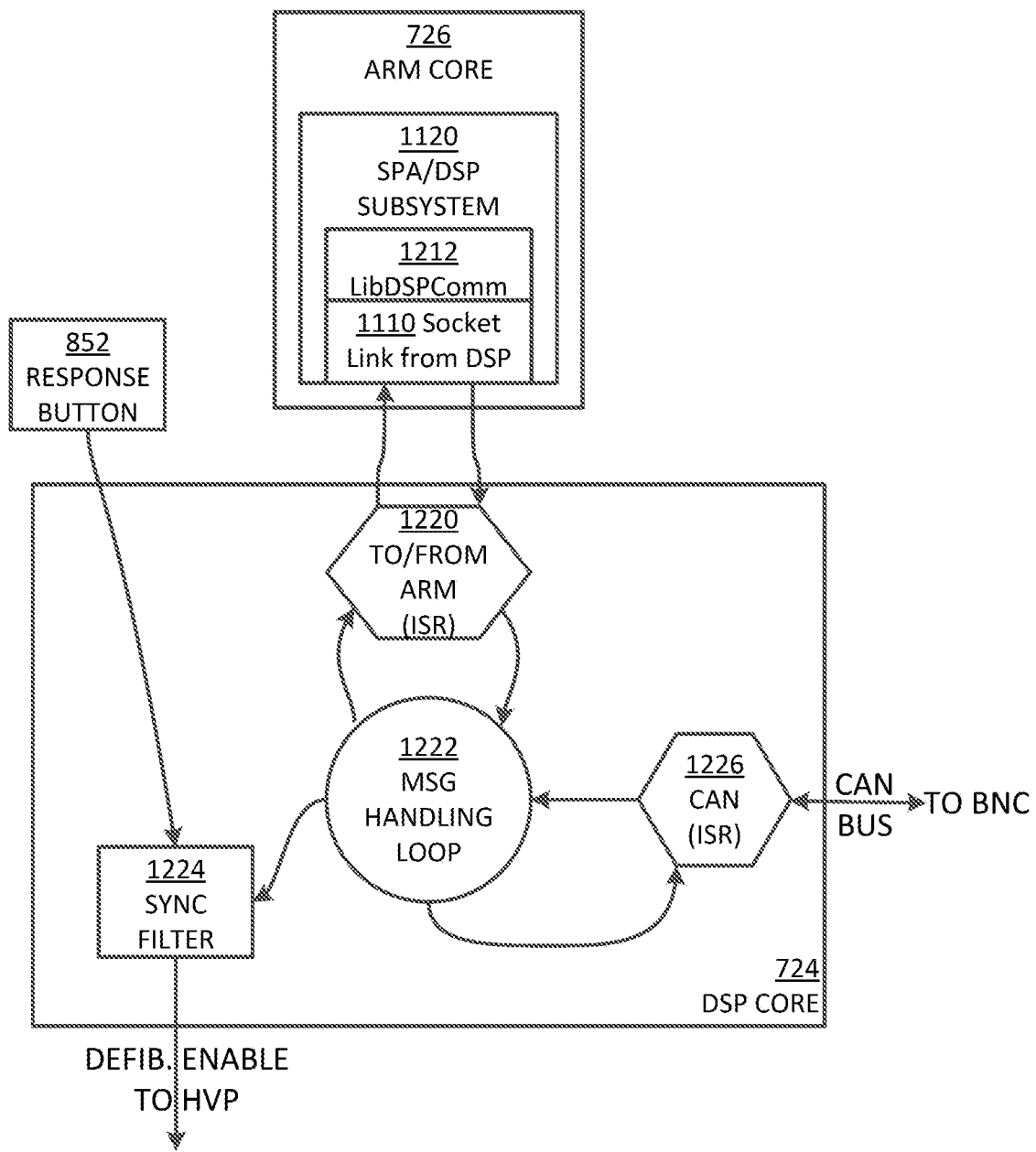
FIG. 12 is a functional block diagram of the DSP core subsystem.

Reference is now made to FIG. 12 showing a functional block diagram of the DSP core subsystem. The DSP core 724 includes a communication subsystem that handles the CAN bus communication in accordance with the techniques disclosed herein. Additionally, in the event of defibrillation, the DSP core 724 is configured to analyze incoming ECG data to synchronize a defibrillation pulse with the R-wave of a patient by transmitting a synchronization control signal. In addition, the DSP core 724 is configured to read inputs from the response button and to instruct delay of pulse delivery when a response button input is received.

The DSP core includes several processing threads in an example, including a to/from ARM thread 1220, a message handling loop 1222 and a CAN thread 1226. The to/from ARM thread 1220 is an Interrupt Service Routine (ISR) that is configured to communicate with the ARM core. There is a DSPLink thread between the DSP core 724 and the ARM Core 726, and there is a dedicated thread for transmitting from the DSP core 724 to the ARM core 726, and a dedicated thread for receiving data from the ARM core 726 at the DSP core 724. The DSPLink driver includes a TI communication library for DSP/ARM interface. The data sent to the ARM core 726 from the thread 1220 includes ECG data and command response. The data received from the ARM core from thread 1220 includes commands. The CAN (ISR) thread 1226 is configured to handle the receipt and transmission of CAN packets with the belt node processor. In some examples, a stand-alone thread is needed since the incoming CAN receiver buffer is one byte. As a result, in these examples, a dedicated thread is needed to ensure data overruns do not occur. The message handling thread 1222 is the primary control thread for the DSP core 724. It is configured to pass all traffic between the ARM and the CAN bus. In one example, this thread is a simple loop that reads CAN packets and transmits them to the ARM core, and reads ARM packets and acts on them. Acting on the ARM packets includes either passing them to the ARM core or doing a local operation (synchronization control signal with the incoming ECG via synchronization filter 1224, or also for example in response to input by the response button 852).

There are four primary interfaces to the DSP core subsystem. The DSPLink to ARM processor interface is used for all DSP core to SPA communications. This is a socketlike interprocess/interprocessor communication interface. All incoming ECG data is passed up to the SPA and CAN and synchronization commands are passed down to the DSP core. The CAN bus interface is the primary mechanism for passing ECG data from the belt to the detection algorithm. There is also a small amount of traffic that goes from the monitor to the belt node module. For example, the gel fire and the general queries are sent from the monitor to the belt.

The Response Button GPIO interface provides an input that indicates whether the patient has actuated one or more response buttons (e.g., the response buttons 852). During execution of a treatment sequence, the DSP core monitors the Response Button GPIO for state changes. If the response button is being pressed (user is delaying treatment), the transmission of the synchronization control signal is delayed and the DSP core notifies the HVP 728 to delay suspend treatment. A synchronization control signal is used when a defibrillation has been commanded and the response buttons are not being held by the patient. The synchronization control signal is sent by the DSP Core to the HVP instructing the HVP when to initiate pulse delivery. If a response button is being held by the patient, the synchronization control signal will not be sent.

Note that in FIG. 12 there is only a single main loop, and there is no multi-processing (i.e., no multiple threads). The SPA/DSP implements a watchdog feature to detect if packets from a connected belt node module stop flowing, and if so, the SPA/DSP can react accordingly. The SPA/DSP also has a communication timeout to detect communication failures and handle the failures appropriately.

Figure 13:
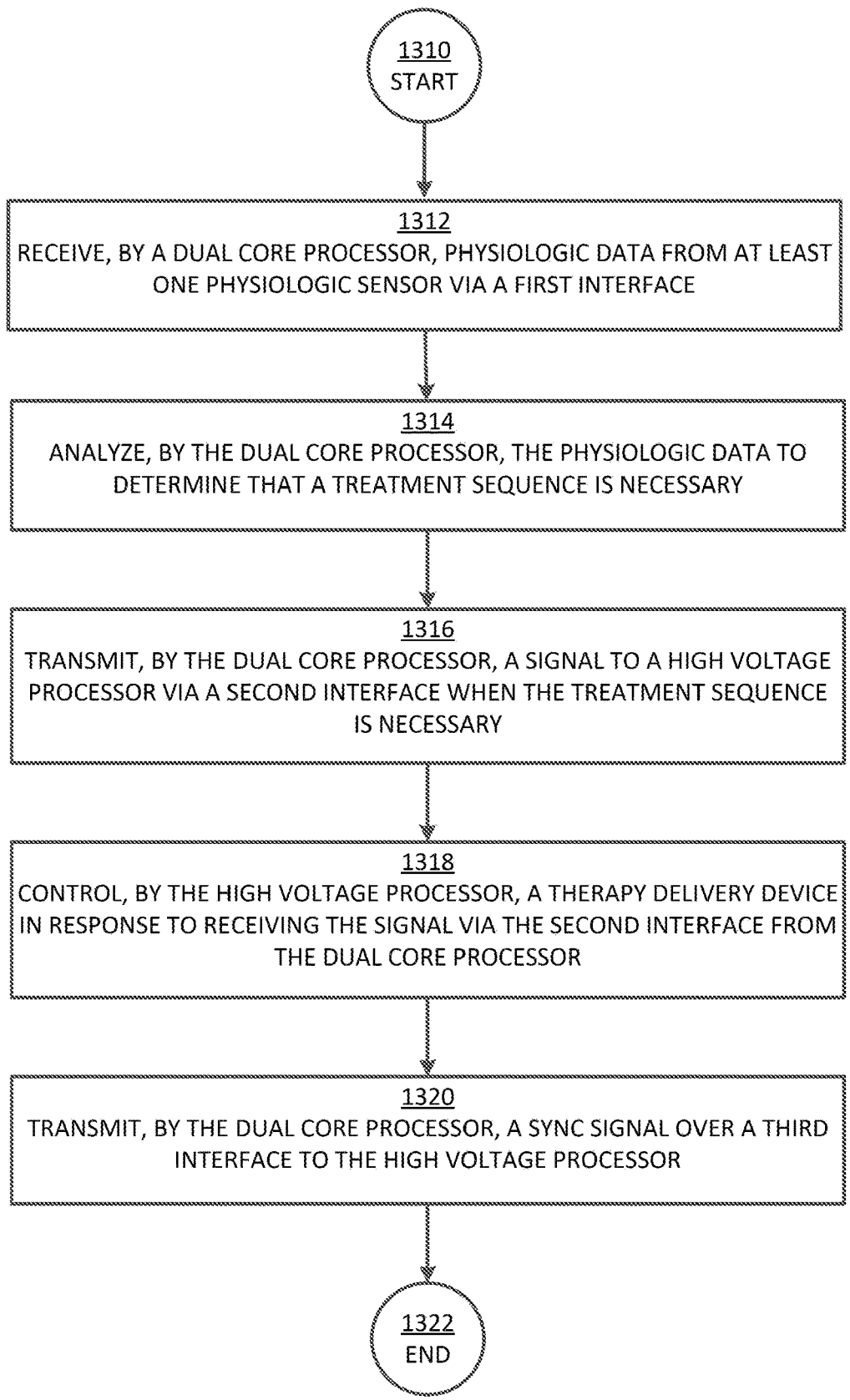
FIG. 13 is a flow diagram of one example of a method for processing physiologic data and delivering treatment using a dual-core processor and a high-voltage processor arrangement.

FIG. 13 is a flow diagram of one example of a method for processing physiologic data and delivering treatment using a dual-core processor and a high-voltage processor arrangement. Various examples provide processes for the operation of the medical device. In these examples, the processor arrangement is designed to segregate the high voltage processing from other system processing, where the other system processing is further segregated by a dual core processor. FIG. 13 illustrates one example treatment process that includes acts of receiving physiologic data, analyzing the physiologic data, transmitting a signal to a high voltage processor, controlling a therapy delivery device and transmitting a synchronization signal. The treatment process begins at 1310.

In act 1312, the dual core processor receives physiologic data from at least one physiologic sensor via a first interface. The first interface path can be, for example, a CAN bus. According to some examples, the physiologic data can be acquired by a physiologic sensor (such as an ECG signal from an ECG sensor) that is digitized by the sensor and transmitted over the first interface to the dual core processor.

In act 1314, the dual core processor analyzes the received physiologic data to determine whether a treatment sequence is necessary. In one example, the DSP core of the dual core processor receives the physiologic data via the first interface (e.g. CAN bus) and transmits the physiologic data to the ARM core. The ARM core can detect a treatable condition in the patient based upon the received physiologic data to indicate to the high voltage processor that a treatment sequence is necessary.

In act 1316, when the dual core processor detects a treatable condition, the dual core processor sends a signal to the high voltage processor via a second interface (e.g. UART). The signal indicates to the high voltage processor that a treatment is imminent. In act 1318, the high voltage processor controls the therapy delivery device in response to receiving a signal via the second communication path from the dual core processor. In act 1320, the dual core processor transmits a synchronization control signal to the high voltage processor over a third interface to provide proper timing of the synchronization control signal. In one example, the synchronization control signal is generated by the DSP core of the dual core processor. The DSP core processes the physiologic data to identify a proper time to deliver the treatment when it has been determined by the ARM core that a treatment is necessary. Once the synchronization control signal has been sent to the high voltage processor, the process ends at 1322.

Various examples of medical devices are disclosed herein. These generally provide a belt node module and a monitor or other control interface. The processor arrangement of the monitor segregates functionality among more than one processor. The dual core processor provides a first processor that is coupled to a therapy delivery device and a control interface. The first processor is configured to control the therapy delivery device to deliver therapy to a patient in response to receiving a signal. The second processor of the dual core processor is distinct from the first processor, and is coupled to a sensor and one control interface. The control interface is configured to receive physiological data from the sensor, process the physiological data to detect a potential condition of the patient, and to transmit data in response to detecting the condition to the first processor. This segregates control of the high voltage processing for treatment from other processing performed by the medical device.

In general summary, examples and aspects of the disclosed herein include a power conserving processor and methods that conserve energy by distributing the execution of instructions across processors with different operating power requirements. While the bulk of the specification discusses this processor architecture in the context of a portable medical device, various aspects disclosed herein may be used in other contexts, such as non-portable medical devices or medical devices that treat abnormalities other than cardiac dysrhythmia. For instance, other abnormalities that may be treated using a portable medical device with a power conserving processor arrangement include epilepsy.

Having thus described several aspects of at least one example, it is to be appreciated various alterations, modifications, and improvements will readily occur to those skilled in the art. Such alterations, modifications, and improvements are intended to be part of this disclosure, and are intended to be within the scope of the examples disclosed herein. In addition, while many examples disclosed herein include two or more physically separate processors, other examples may be implemented on a single, multi-core processor with one core functioning as the critical purpose processor 104 and another core functioning as the general purpose processor 102. Other examples may employ three or more processors, each dedicated to a particular set of critical or non-critical functions. Moreover, while many examples include a dual core processor having an ARM core and a DSP core, any dual core or multi-core processor can be implemented in accordance with the techniques herein, for example a multi-core processor having at least one application core and at least one signal processing core. Accordingly, the foregoing description and drawings are by way of example only.

What is claimed is:
1. A therapeutic medical device comprising:
   a cardiac sensing electrode configured to receive electrocardiogram (ECG) data indicative of cardiac activity of a patient;
   a therapy delivery device that includes a therapy pad and an electrically conductive gel;

a user interface configured to provide a stimulus to the patient, wherein the stimulus is at least one of a visual, aural, or tactile stimulus;
a multicore processor comprising:
a first processor core configured to detect an arrhythmia condition based on the cardiac activity of the patient, generate a service request that is responsive to the detected arrhythmia condition, and initiate a treatment of the arrhythmia condition using the therapy delivery device, and
a second processor core that is configured to receive the service request from the first processor core and control the user interface to provide the stimulus to the patient; and
a node that is coupled to the multicore processor, the therapy delivery device, and the cardiac sensing electrode, wherein the node transmits a gel application signal to the therapy delivery device,
wherein, responsive to receiving the gel application signal, the therapy delivery device is configured to apply the electrically conductive gel between the therapy pad and the patient.

2. The therapeutic medical device of claim 1, wherein the therapy delivery device is configured to apply the electrically conductive gel before the treatment is initiated.

3. The therapeutic medical device of claim 1, wherein the user interface is further configured to receive, from the patient, a response to the stimulus.

4. The therapeutic medical device of claim 3, wherein the second processor core is further configured to, based on the user interface receiving the response, instruct the first processor core to delay or cancel the treatment.

5. The therapeutic medical device of claim 1, wherein the second processor core is further configured to control the user interface to generate an audible announcement that warns bystanders to step back from the patient.

6. The therapeutic medical device of claim 1, wherein:
the multicore processor is positioned within a monitor; and
the node is connected between the monitor and the therapy delivery device.

7. The therapeutic medical device of claim 6, wherein the monitor further includes the user interface.

8. The therapeutic medical device of claim 1, wherein further comprising a shared memory configured to communicate with at least one of the first processor core or the second processor core and to store physiologic data representative of the cardiac activity of the patient.

9. The therapeutic medical device of claim 1, wherein the first processor core is a digital signal processor core and the second processor core is an advanced RISC machine core.

10. The therapeutic medical device of claim 1, wherein the node includes a belt node processor.

11. The therapeutic medical device of claim 10, wherein:
the node further includes a tactile alarm; and
responsive to a control signal received from the first processor core, the belt node processor controls the tactile alarm to provide the tactile stimulus to the patent.

12. The therapeutic medical device of claim 10, further comprising a heart sounds sensor configured to generate heart sounds data of the patient, wherein the belt node processor is configured to collect the heart sounds data and transmit the heart sounds data to the second processor core.

13. The therapeutic medical device of claim 10, wherein:
the node further comprises a signal acquisition circuit that acquires the ECG data from the cardiac sensing electrode and generates ECG signals; and
the first processor core detects the arrhythmia condition based on the ECG signals generated by the signal acquisition circuit.

14. The therapeutic medical device of claim 13, wherein the belt node processor runs a scheduling loop that iteratively acquires the ECG data from the cardiac sensing electrode and transmits the ECG signals to the first processor core.

15. The therapeutic medical device of claim 1, wherein:
the second processor core is configured to adjust a treatment timeline based on patient input provided via the user interface; and
the first processor core initiates the treatment based on the adjusted treatment timeline.

16. The therapeutic medical device of claim 1, wherein:
the node includes an accelerometer configured to generate motion data indicative of movement of the node;
the second processor core is configured to adjust a treatment timeline based on the motion data; and
the first processor core initiates the treatment based on the adjusted treatment timeline.

17. The therapeutic medical device of claim 1, further comprising high voltage circuitry that is in communication with the first processor core and that is capable of delivering a biphasic defibrillation pulse having a pulse energy in the range of 75 joules to 150 joules to the therapy delivery device.

18. The therapeutic medical device of claim 17, wherein the first processor core is configured to control the pulse energy in the biphasic defibrillation pulse.

19. The therapeutic medical device of claim 1, wherein:
the node further comprises a signal acquisition circuit that acquires the ECG data from the cardiac sensing electrode and generates ECG signals; and
the second processor core is further configured to communicate data representative at least a portion of the ECG signals via wireless communication to an external source.

* * * * *